US008603965B2

(12) United States Patent
Zhou et al.

(10) Patent No.: US 8,603,965 B2
(45) Date of Patent: Dec. 10, 2013

(54) PHARMACEUTICAL COMPOSITION FOR THE PROPHYLAXIS AND TREATMENT OF HIV INFECTION AND ITS USE

(75) Inventors: Genfa Zhou, Tianjin (CN); Qing Liang, Tianjin (CN); Dan Ju, Tianjin (CN)

(73) Assignee: FusoGen Pharmaceuticals, Inc., Tianjin (CN)

( * ) Notice: Subject to any disclaimer, the term of this patent is extended or adjusted under 35 U.S.C. 154(b) by 1290 days.

(21) Appl. No.: 12/304,690

(22) PCT Filed: Jun. 12, 2007

(86) PCT No.: PCT/CN2007/001849
§ 371 (c)(1),
(2), (4) Date: Dec. 12, 2008

(87) PCT Pub. No.: WO2007/143934
PCT Pub. Date: Dec. 21, 2007

(65) Prior Publication Data
US 2009/0203600 A1    Aug. 13, 2009

(30) Foreign Application Priority Data

Jun. 12, 2006  (CN) .......................... 2006 1 0014314
Dec. 1, 2006   (CN) .......................... 2006 1 0160758

(51) Int. Cl.
    *A61K 38/00*          (2006.01)
(52) U.S. Cl.
    USPC .............................. 514/1.1; 514/3.7; 514/3.8
(58) Field of Classification Search
    None
    See application file for complete search history.

(56) References Cited

U.S. PATENT DOCUMENTS

| 6,962,900 B2 | 11/2005 | Zhou et al. |
| 7,335,727 B2 | 2/2008 | Zhou et al. |
| 2010/0021427 A1 | 1/2010 | Chen et al. |

FOREIGN PATENT DOCUMENTS

| CN | 1100564 C | 2/2003 | |
| EP | 0579363 A1 | 1/1994 | |
| EP | 1421946 * | 5/2004 | ........... A61K 31/496 |
| EP | 1421946 B1 | 8/2006 | |
| HK | 1067531 | 1/2009 | |
| JP | 63-107924 A | 5/1988 | |
| JP | 2004538334 | 12/2004 | |
| RU | 2290197 C2 | 12/2006 | |
| SG | 102967 | 1/2006 | |
| WO | 87/07613 A1 | 12/1987 | |
| WO | 94/27590 A1 | 12/1994 | |
| WO | 96/19495 A1 | 6/1996 | |
| WO | 99/59615 A1 | 11/1999 | |
| WO | 01/03723 A1 | 1/2001 | |

(Continued)

OTHER PUBLICATIONS

Lalezari, et al. A phase II clinical study of the long-term safety and antiviral activity of enfuvirtide-based antiretroviral therapy. AIDS 2003; 17:691-698.*

(Continued)

*Primary Examiner* — Jeffrey Stucker
*Assistant Examiner* — Stuart W Snyder
(74) *Attorney, Agent, or Firm* — Duan Wu, Esq.; Milstein Zhang & Wu LLC (57) ABSTRACT

Pharmaceutical compositions for the prophylaxis and treatment of HIV infection and its use are provided. Particularly, the present invention provides a pharmaceutical composition comprising anti-virus peptides, use of said composition for manufacturing a medicament for the prophylaxis and treatment of HIV infection, and method for preventing and treating HIV infection by using said composition.

27 Claims, 2 Drawing Sheets

(56) References Cited

FOREIGN PATENT DOCUMENTS

| WO | 01/44286 A2 | 6/2001 |
|---|---|---|
| WO | 01/51673 A2 | 7/2001 |
| WO | 2003018045 A1 | 1/2010 |

OTHER PUBLICATIONS

Morris, et al. A lysine to arginine substitution at position 146 of rabbit aldolase A changes the rate-determining step to Schiff base formation. Protein Engineering. 1996; 9(1): 61-67.*
Perrin, L. et al., "HIV Treatment Failure: Testing for HIV Resistance in Clinical Practice," Science, vol. 280 (1998) 1871-73.
Gan. Y., et al. "Solid Phase Peptide Synthesis of Fusukang for AIDS." Transactions of Tianjin University, Dec. 2003, vol. 9, No. 4 (China) pp. 289-291.
Dai, S., et ai. "Quantification of sifuvirtide in monkey plasma by an on-line solid-phase extraction procedure combined with liquid chromatography/electrospray ionization tandem mass spectrometry." Rapid Commun. Mass Spectrom. 2005:19(10):1273-82. Published online (www.interscience.wiiey.com).
DAl, S., et al. "Pharmacokinetics of sifuvirtide. a novel anti-HIV-1 peptide, in monkeys and its inhibitory concentration in vitro," Acta Pharmacologica Sinica Oct. 26, 2005(10): 1274-80 (China).
Lui, D., et al. "Pharmacokinetics of [1251] sifuvirtide in rats," Chin J Pharmacol Toxicol (China) Aug. 25, 2005; 19(4): 296-299 (China) (English Abstract at the end).
Liu, D., et al. "Determination of Suluvirtide Concentration by 1251 Tracer Labeling Method, " Journal of Isotopes (China) Nov. 2006: 19 (4): pp. 228-232 (China).
Guo, Y., et al. "Sythesis of Fuskukang by solid-phase sythesis, " Journal of Chemical and Engineering (China) 58(1): pp. 200-204, Jan. 2007 (China).
Franquelim, H., et al. "Sifuvirtide screens rigid membrane surfaces. establishment of a correlation between efficacy and membrane domain selectivity among HIV fusion inhibitor peptides, " J Am Chem Soc, 130: 6215-23 (Published on Web Apr. 15, 2008).
He, Y., et al. "Design and evaluation of sifuvirtide. a novel HIV-1 fusion inhibitor," J Biol Chem (Apr. 25, 2008), 283(17): 11126-34 (United States).
Dong, X. et al "N-and C-domains of HIV-1 gp41: mutation, structure and functions," Immunology Letters 75 (2001) 215-220.
Ferrer, M. et al "Selection of gp41-mediated HIV-1 cell entry inhibitors from biased combinatorial libraries of non-natural binding elements," Nature Structural Biology, Oct. 1999, vol. 6, 953-960.
Nippon Rinsho, "HIV Infection . AIDS" Sep. 1993, An extra issue for 1993.
Jiang, S. et al "Effect of Amino Acid Replacements, Additions and Deletions on Antiviral Activity of a Peptide Derived from the HIV-1 GP41 Sequence" Peptide Research, Dec. 1995, vol. 8, 345-348.
Chan, D. et al "Evidence that a prominent cavity in the coiled coil of HIV type 1 gp41 is an attractive drug target" Proc. Natl. Acad. Sci. USA, Dec. 1998, vol. 95, 15613-15617.
Kliger, Y. et al "Inhibition of HIV-1 Entry Before gp41 Folds Into its Fusion-active Conformation" J Molecular Biology, Jan. 14 2000, vol. 295, 163-168.
Mobley, P. et al "Membrane-pertubing domains of HIV Type 1 Glycoprotein 41" AIDS Research and Human Retroviruses, vol. 17, Nov. 2001, 311-327.
Scholtz, M. et al. "The mechanism of a-helix formation by peptides" Annu. Rev. Biophys. Biomol. Struct. 1992, vol. 21, 95-118.
Marqusee, S. et al "Helix stabilization by Glu- . . .Lys+ salt bridges in short peptides of de novo design" Proc. Natl. Acad. Sci. USA, Dec. 1987, vol. 84, 8898-8902.
Wild, C. "Peptides corresponding to a predictive a-helical domain of human immunodeficiency virus type 1 gp41 are potent inhibitors of virus infection" Proc. Natl. Acad. Sci. USA, 1994, vol. 91, 9770-9774.
Wild, C. "A synthetic peptide inhibitor of human immunodeficiency virus replication: Correlation between solution structure and viral inhibition" Proc. Natl. Acad. Sci. USA, 1992, vol. 89, 10537-10541.

* cited by examiner

SEQUENCE LISTING

<160> NUMBER OF SEQ ID NOS: 1

<210> SEQ ID NO 1
<211> LENGTH: 36
<212> TYPE: PRT
<213> ORGANISM: homo sapiens
<220> FEATURE:
<221> NAME/KEY: HIV
<222> LOCATION: (1)..(36)
<223> OTHER INFORMATION: HIV gp41

<400> SEQUENCE: 1

Ser Trp Glu Thr Trp Glu Arg Glu Ile Glu Asn Tyr Thr Arg Gln Ile
1               5                   10                  15

-continued

```
Tyr Arg Ile Leu Glu Glu Ser Gln Glu Gln Gln Asp Arg Asn Glu Arg
                20                  25                  30
Asp Leu Leu Glu
    35
```

PHARMACEUTICAL COMPOSITION FOR THE PROPHYLAXIS AND TREATMENT OF HIV INFECTION AND ITS USE

FIELD OF THE INVENTION

This invention relates to pharmaceutical compositions containing effective amounts of antiviral peptides which are used to prevent or treat HIV infection, and the use of such compositions in producing pharmaceuticals for the prevention and treatment of HIV infection.

BACKGROUND OF THE INVENTION

1. HIV and AIDS Epidemic

Infection with Human Immunodeficiency Virus (HIV), a pathogenic retrovirus, can cause Acquired Immunodeficiency Syndrome (AIDS) (Barre-Sinossi, F. et al. SCIENCE. 220: 868-870 (1983)). Although macrophage, neuron and other cells can be infected by HIV (Maddon et al. CELL. 47:333-48 (1986)), the CD4+ lymphocytes are the major target cells for HIV (Dalgleish, A. et al. NATURE; 312:767-8 (1984)), because HIV has strong affinity to the CD4 molecules on the surfaces of CD4+ cells. HIV infection in a human body destroys so many CD4+ lymphocytes that the body begins to lose its immune function, therefore an AIDS patient is highly vulnerable to various infections, neuronal dysfunction, tumors, and so on. Suffering from the infections, patients die eventually (Levy, J. A., ed., ACUTE HIV INFECTION AND SUSCEPTIBLE CELLS, p 63-78, published in U.S.A, 2000).

With its severe symptoms and high mortality rate, the epidemic contagion of AIDS has become one of the leading causes of death that is threatening human health. So far in the entire world, people infected by HIV have accumulated to a total of 39,500,000. In 2006 alone, 2,900,000 people died from AIDS and 4,300,000 people became infected by HIV. In China, HIV infection has been spreading rapidly. In China, an estimated 650,000 were living with HIV at the end of 2005. It is estimated that half the new infections in 2005 occurred during unprotected sex. With HIV spreading gradually from high-risk populations to the general population, the number of HIV infections in women has been growing too (WHO REPORT 2006, UNAIDS and WHO).

Currently, at least two types of HIV have been identified: HIV-1 (Gallo, R. et. al. Science 224:500-503 (1984)) and HIV-2 (Clavel, F. et al. Science 223: 343-346 (1986)). Each of them has high genetic heterogeneity. For HIV-1 alone, there are at least 11 different genotypes (A-J and O subtypes) (Jonassen, T. O. et al. Virol. 231:43-47 (1997)). The E subtype of HIV-1 is distributed mainly in Central Africa, Thailand, India, Vietnam, Kampuchea, Malaysia, Burma, China, and the Western Hemisphere (WHO REPORT 1996). The HIV subtypes found in China are mostly B, E, or C subtypes (Yu, E. S. et al. American J. Public Health. 86 (8 Ptl): 1116-22 (1996)).

The reproduction cycle of HIV has several important steps. First, the envelope glycoprotein gp120 of virus attaches to the host cell membrane through its specific binding with CD4+ molecule located on the surface of T4 lymphocyte. With the assistance of a series of chemokine co-receptors, the viral envelope fuses with the host cell membrane (Berger, E. A., et al. Ann. Re. Immunol. 17: 657-700 (1999)). After the fusion process, the HIV virion packed in nucleocapsid enters the host cell with its capsid shucked off and viral nucleic acid exposed. The viral reverse transcriptase catalyzes the reverse transcription of HIV single-stranded RNA into single-stranded DNA, which is then turned into double-stranded DNA with the help of cellular polymerase. The double-stranded DNA can either exist freely in cytoplasm or be integrated as provirus into host chromosome DNA by the catalysis of viral integrase, thus engendering HIV latent infection (Roe, T. et al. J. Virol. 71(2): 1334-40 (1997)). Provirus, which is not excised from the host chromosome, is stable and reproduces itself with the replication of host chromosome. After the HIV mRNA is translated into a large polyprotein, the viral proteases cut and process the polyprotein to form mature viral structural proteins (Xiang, Y. & Leis, J. J. Virol. 71(3):2083-91 (1997)). These structural proteins, together with HIV nucleic acids, are finally assembled into new virus granules and released outside the cell through a budding process (Kiss-Lazozlo, Hohn, T. Trends in Microbiology 4(12):480-5 (1996)).

In sum, the critical stages of HIV replication are: 1) virus attachment and entry into host cell through a fusion process; 2) reverse transcription and integration; 3) protein translation and processing; 4) virus assembly and release.

2. Treatment for HIV Infection

Although great efforts have been dedicated to effective medicines and preventive methods for many years, there is no working vaccine or cure for AIDS yet.

An ideal vaccine should be non-toxic, and capable of inducing neutralizing antibodies as well as persistent immune responses in mucous membrane and blood (Levy, J. A. and Levy, J. A. Trens Med. Rev. 2: 265-71 (1988)). Most HIV vaccines currently developed in the world are still in the stage of animal study. Although vaccine against HIV membrane proteins gp160 and gp120 have already moved into clinical trials, the results are disappointing. The vaccine is effective to prevent HIV infection in laboratory, but not work in HIV strains isolated from human (McElrath, M. J. et al. Pro. Natl. Acad. Sci. USA. 93: 3972-77 (1996)). Little progress made in HIV vaccine research could be attributed to the complexity and variability of HIV genetic materials (Bloom, B. R. Science 272: 1888-1900 (1996)).

Drugs against AIDS approved in the world could be classified into two categories: HIV reverse transcriptase inhibitor (Charles, C. J., et al. JAMA 276:146 (1996)) and HIV protease inhibitor (Miles, S. A. et al., International AIDS Society USA 4(3):15). Both of them aim at later stages of HIV infection—transcription and assembly of new virus. The well-known "Cocktail Therapy" is a combination therapy utilizing both types of inhibitors (Lafeuillade, A., et al. J. Infect. Dis. 175:1051-55 (1997)).

Reverse transcriptase inhibitors, including AZT, ddI, ddC, 3TC, and d4T, etc, would induce drug resistance, sooner or later, that means the viruses become less sensitive to the drug, and the effective inhibition concentration of the drug rise by several-fold or even ten-fold (Vella, S, and Floridia, M. International AIDS Society USA 4 (3): 15 (1996)). This drug-resistance is associated with high mutation rate of HIV. In a human body, a single HIV virus could produce 108-1010 new virus granules every day, while the mutation rate is 3 per replication cycle. Many mis-sense mutations, affecting the expression of amino acids, may happen in the regulatory genes as well as in the envelope proteins. In some HIV strains, the mutation rate could be as high as 40% in the amino acid sequences of certain genes (Myers, G and Montaner, J. G. The Retroviridae vol. 1, Plenum Press, New York 51-105 (1992)). As a result, drug-resistance develops by suppressing of sensitive strains by reverse transcriptase inhibitors which facilitates the proliferation of resistant strains that exist before and after the mutations.

Moreover, all the reverse transcriptase inhibitors have specific toxicity related to their dosage. The symptoms include spinal cord suppression, vomiting, liver dysfunction, muscle weakness, diseases of peripheral nervous system, and pancreatic inflammation. Many patients have to suspend the treatment due to these intolerable side effects (Fischl, M. A., et al. N. Engl. J. Med. 317: 185-91 (1987); Lenderking, W. R., et al. N. Engl. J. Med. 330:738-43 (1994)).

Drug-resistance is also a problem for protease inhibitors. Mutations in the viral protease gene have caused drug-resistance in all the protease inhibitors presently used in AIDS treatment (Condra, J. H. et al. Nature. 1995; 374:569-71). Side effects of protease inhibitors include liver dysfunction, gastrointestinal discomfort, kidney stone, numbness around mouth, abnormality of lipid metabolism, and mental disorder (Deeks, et al. JAMA 277:145-53 (1997)).

In sum, most of the currently used anti-HIV drugs are highly toxic, and induce drug-resistance. Therefore, there is still a huge obstacle in the treatment of HIV infection. Apparently, it is urgent for the need of new drugs with better efficacy and lower toxicity for the treatment of HIV infection.

New drugs can be developed against new targets in different stages of HIV replication cycle. Recently, a few anti-HIV drugs with new mechanisms have been developed after in-depth research in HIV and AIDS. These drugs include some new HIV reverse transcriptase inhibitors and HIV protease inhibitors, as well as some new anti-HIV agents aimed at other targets that are listed hereinafter (De, C. E. Rev. Med. Virol. 10(4):255-77 (2000)):

1. Virus absorbent, such as sodium lauryl sulfate, dextrose sulfate, and heparin, which can interrupt the cohesion between gp120 on HIV envelope and lymphocyte through the action of their polyanion groups. However, these absorbents have low specificity and high toxicity. Some of them can even increase the virus load (Baba, M., et al. Pro. Natl. Acad. Sci. USA. 85:6132-6 (1988));

2. Soluble CD4 can be used to prevent gp120 from binding to host cells. Some recombinant soluble CD4 could bind to virus granules before gp120 contact the CD4 molecules on cellular membrane, which may prevent HIV infection. However, these recombinant soluble CD4 are of no apparent effect on the HIV-1 strains isolated from some patients. Moreover, the clinical experiments did not provide any reliable evidence for their antiviral activity (Gomatos, P. J. et al. J. Immunol. 144:4183-8 (1990));

3. Chemokines and their analogs, including RANTES, MIP-1α, MIP-1β binding with CCR5 and SDF binding with CXCR4, can be used to prevent HIV from entering the host cells. They could not only competitively block the gomphosis between HIV gp120 and cellular chemokine co-receptors but also limit HIV inbreak points by depressing the expression of these co-receptors on cell. The latest chemokine co-receptor blockers include positive charged small peptides such as ALX40-4C and T22, and compounds such as AMD3100, TAK-779 and trichosanthin;

4. Although soluble CD4-IgG can suppress HIV replication in vitro, it has no reliable antiviral activity in clinical trials;

5. Agents such as 2,2'-dithiobisbenzamides (DIBAs) and azadicarbonamide (ADA) can block the assembly and disassembly of viruses through interactions with NCp7 zinc finger site;

6. A segment of gp41 or its analog can be used as a fusion inhibitor. For example, T-20 is capable of blocking virus entry into the cell (Jiang, S. et al., Nature 365:113 (1993));

7. Inhibitors of viral mRNA transcriptase, such as CGP64222, fluoroquinolone K-12, and EM2487;

8. Inhibitors of integrase, such as derivatives of Carbonyl J [N,N'-bis(2-(5-hydroxy-7-naphthalenesulfonic acid)urea], can prevent HIV from integrating its genome into host lymphocyte genome (Maurer K, et al., Bioorg Chem 28(3):140-155 (2000)).

3. Fusion Inhibitors that Block Viral Entry into Cells

Many biological processes involve membrane fusion. In eukaryotic cell, fusion of cellular membranes is happening continuously, including endocytosis, secretion, recycle of membranous components and so on (White J. M., Science 258:917-24 (1992)). Examples of fusion in some peculiar cells include the secretion of regulated fusion hormone, enzyme, and nerve transmitter. Some more notable examples include the fusion between germ cell and ovum, and of muscle cells.

In conclusion, membrane fusion is a critical step for envelope virus to attack and penetrate the host cells (Weissenhorn, W., et al. Nature 387: 426-30 (1997)). The fusion process is controlled by the glycoproteins on HIV envelope. The precursor of the glycoproteins is gp160 that has polysaccharide groups. During the virus reproduction period, gp160 is hydrolyzed by host protease into two subunits: gp120 anchoring outside the envelope and trans-membrane protein gp41. After the hydrolyzation, gp120 and gp41 are still linked by non-covalent bond and polymerized as trimers outside the virus granule. The trans-membrane protein gp41, whose ectodomain with a highly helical structure, has a highly efficient origination mechanism for membrane fusion, and is known as the pivotal molecule to open the gate of cells for its direct participation in the fusion process (Ferrer, M., et al. Nat. Struct. Biol. 6(10): 953-60 (1999); Zhou, G., et al. Bioorg. Med. Chem. 8(9): 2219-27 (2000)).

Crystal diffraction analyses have shown that when fusion takes place between the HIV virus and the cell, the core of gp41 consists of six helical bundles wherein the N-terminal and C-terminal helices are collocated as three hairpins which fix the HIV envelope to the cellular membrane. The gp41 trimer can form a fusion pore that facilitates the viral intrusion into the host cell (Chan, D. C., et al. Cell 89: 263-73 (1997)). Gp41 exists in an unstable natural non-fusion conformation on the surface of the free virus particle fresh sprouting from infected cells. At first, the N-terminal helices are wrapped inside the C-terminal helices so that the N-terminal fusion area is hidden, then after gp120 on viral surface combines with the CD4 receptor and chemokine co-receptors on the cell membrane, a receptor-activated conformational change of gp41 occurs wherein its N-terminal extends beyond the viral surface into the host cellular membrane. At this time, gp41 is transformed from an unstable natural non-fusion conformation into a pre-hairpin intermediate conformation. When the C-terminal and N-terminal of gp41 peptides bind together, the hydrophobic N-terminal core of the trimer structure is exposed, and the pre-hairpin intermediate is transformed into a more energy-stabilized hairpin conformation, and by this time the viral envelope has fused with the cellular membrane (Jones, P. L., et al. J. Biol. Chem. 273: 404 (1998)).

According to an embodiment of the present invention, the anti-fusion or anti-membrane fusion is to inhibit or suppress the fusion of two or more biological membranes. According to an embodiment of the present invention, two or more biological membranes are either cellular or viral structures, such as cell membrane and viral envelope. According to an embodiment of the present invention, the anti-fusion agent or anti-membrane fusion agent is a substance that inhibits the viral infection from cells, such as inhibit the fusion of cell and viral envelope or inhibit fusion of cells.

The first-discovered fusion inhibitor is a 36 amino-acid peptide derived from the C-terminal (127-162) of gp41 - - - T-20, its sequence is as follows:

X-YTSLIHSLIEESQNQQEKNEQELLELDKWASLWNWF-Z.

The structural similarity of T-20 to the C-terminal of gp41 makes it capable of competing with the C-peptide of gp41 in binding with its N-terminal fusion domain. On the surface of T-cell, T-20 at very low concentration can interrupt the fusion between HIV gp41 and host cell membrane (the $IC_{50}$ is within the range of nM) (Jiang, S., et al. Nature 365:113 (1993); Wild, C. T. et al., Pro. Natl. Acad. Sci. USA 91: 9770-74 (1994)). In the pre-hairpin state which lasts for minutes, T-20 is very effective in inhibiting the binding of the C-peptide of gp41 with its N-terminal fusion domain, thus blocking the formation of a hairpin between the viral envelope and cell membrane (Kliger, Y and Shai, Y, J. Mol. Biol. 295:163-8 (2000)).

Because fusion inhibitors act on the cellular membrane, they do not need to be released inside cell to exert their functions. In comparison, anti-HIV drugs that are currently in clinical use all act in the middle or late stages of viral infection of host cell. That means they must be first released into the cell to be able to inhibit the reproduction of the invading HIV. In addition, the highly conserved amino acid sequence of the hydrophobic core of gp41 suggests that the virus is not likely to develop drug resistance against the fusion inhibitor. It has been shown in in vitro experiments that T-20 can specifically block HIV entry into cells. On the other hand, clinical trials have indicated that T-20 is well tolerated in AIDS patients, has no toxicity on the spinal cord, and the most common side effects are slight or moderate. Administration by 200 mg of T-20 daily can remarkably reduce the HIV load in most patients, wherein 30% has undetectable HIV load (lower than 400 c/mil). Besides, T-20 is also effective in HIV patients who have already developed drug resistance. It is reported that the number of CD4+ cells in some patients increased after use of T-20 (Kilby, J. M. et al., Nat. Med. 4:1302-1307 (1998)). There has been the concern that long-term administration of T-20 might induce the T-20 specific antibodies that might cause resistance to T-20 in AIDS patient. Nevertheless, during the experiment for dozens of weeks, T-20 maintained its antiviral activity all the time (Pilcher, C. D. et al., AIDS. 13(15): 2171-4 (1999)).

Compared to HIV reverse transcriptase inhibitors and protease inhibitors currently in clinical use, advantages of the fusion inhibitor T-20 are: better efficacy, lower toxicity, and no drug resistance yet. However, the clinical dosage of T-20 as high as 200 mg per day is an indication of its relatively poor stability and low anti-fusion valence. In addition, because of such high dosage, T-20 has caused some local reaction in some patients (Kilby, J. M. et al., Nat. Med. 4:1302-1307 (1998)).

Due to the unmet need of T-20 aforementioned, people developed other novel fusion inhibitors with improved characteristics. A peptide used for treating HIV infection is published in co-owned Chinese Patent CN01130985.7, which is derived from the amino acid residues 117-151 of the C-terminal of HIV-1 (E subtype) transmembrane protein gp41. The amino acid sequence of the peptide is: X-SWETW-EREIENYTKQIYKILEESQEQQDRNEKDLLE-Z. It is reported that the EC50 of the peptide is 20 times lower than T-20 in an HIV fusion assay.

However, there is still a need for new, more stable, higher efficacy, and lower toxicity antiviral drugs, especially HIV fusion inhibitor and more safe and effective drug and method to prevent and treat HIV infection.

SUMMARY OF THE INVENTION

The present invention provides novel pharmaceutical compositions for preventing or treating HIV infection where the antiviral peptide is a membrane fusion inhibitor. Because it takes action outside cells and targets viral protein, the side effects are lower than traditional antiviral agents. In comparison to aforementioned T-20, the antiviral peptide of the present invention has higher potency and longer half-life. This leads to lower dose, lower side effects and longer administration intervals which can decrease financial burden of the patients and improve patient compliance.

The present invention provides novel pharmaceutical compositions for preventing or treating HIV infection comprising effective amounts of antiviral peptide and pharmaceutical acceptable carrier, excipient, diluent and other supplemental agents. The antiviral peptide includes the amino acid sequence of: SWETWEREIENYTRQIYRI-LEESQEQQDRNERDLLE (SEQ ID NO:1). This pharmaceutical composition can be administered by injection, oral, mucosa, rectal or transdermal routes. According to an embodiment of the present invention, the dosage form can be sterile injection powder or lyophilized injection powder. This pharmaceutical composition can include other anti-HIV therapeutic agents.

In one aspect, the present invention is directed to a pharmaceutical composition comprising a therapeutically effective amount of a peptide that includes the amino acid sequence of SEQ ID NO: 1. In another aspect, the present invention is directed to a pharmaceutical composition comprising a therapeutically effective amount of a peptide that includes a conservatively modified variant of the amino acid sequence of SEQ ID NO: 1. In one feature, the peptide sequence is:

X- SWETWEREIENYTRQIYRILEESQEQQDRNERDLLE -Z, where "X" may represent an amino group, a hydrophobic group, including but not limited to carbobenzoxyl, dansyl, or tert-butyloxycarbonyl; an acetyl group; 9-fluorenylmethoxy-carbonyl (FMOC) group; a macromolecular carrier group including but not limited to lipid fatty acid conjugates, polyethylene glycol, or carbohydrates. "Z" may represent a carboxyl group; an amido group; a tert-butyloxycarbonyl group; a macromolecular carrier group including but not limited to lipidfatty acid conjugates, polyethylene glycol, or carbohydrates.

In another embodiment, the inventive composition further includes one or more antiviral agents, such as one selected from reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, γ-interferon, and other anti-HIV agents.

In yet another aspect, the present invention is directed to a method for preparing a pharmaceutical composition, the method comprising adding to the composition a peptide comprising the amino acid sequence of SEQ ID NO: 1, or a conservatively modified variant thereof. Other antiviral agents, such as those described in the paragraph above, may also be added to the composition.

Also, the present invention further provides a method for preventing or treating at least one viral infection, e.g., HIV infection, including administering the pharmaceutical composition containing effective amount of antiviral peptide with amino acid sequence of SEQ ID NO: 1, or a conservatively modified variant thereof, or containing a mixture of the antiviral peptide aforementioned and other anti-HIV therapeutic agents. In one embodiment, the medication is administered no more frequently than once a day. The second anti-HIV agent may be selected from reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, γ-interferon, and other known anti-HIV agents. In one feature, the method further includes the step of selecting the patient whose viral load is below a clinically acute level. In one embodiment, the patient selected to receive medication has a viral load at or below 30,000 c/ml in his blood. In one embodiment, the peptide is administered in a manner selected from the group consisting of intramuscular, intravenous, subcutaneous, oral, mucosal, rectal and percutaneous administration.

BRIEF DESCRIPTION OF THE DRAWINGS

The foregoing, and other features and advantages of the invention, as well as the invention itself, will be more fully understood from the description, drawings and claims that follow. The drawings are not necessarily to scale, emphasis instead generally being placed upon illustrating the principles of the invention.

DETAILED DESCRIPTION OF THE INVENTION

According to the aforementioned, the present invention provided a pharmaceutical composition for preventing or treating HIV infection. The composition contains an effective amount of antiviral peptide as HIV fusion inhibitor and pharmaceutical acceptable carrier, excipient, diluent and other supplemental agents. The amino acid sequence of the antiviral peptide is:

```
                                        (SEQ ID NO: 1)
        SWETWEREIENYTRQIYRILEESQEQQDRNERDLLE.
```

According to the antiviral principal of the aforementioned inventive antiviral peptide, the active part of the peptide is the 36 amino-acid sequence (SEQ ID NO: 1). Thus, the peptide can be conservatively modified according to methods well known to one skilled in the art to the extent that the modification doses not destory α-helics, but can increase the stability, bioavailability or activity of the peptide.

Thus, the present invention is directed to a pharmaceutical composition comprising a therapeutically effective amount of a peptide that includes a conservatively modified variant of the amino acid sequence of SEQ ID NO: 1. The amino acid sequence of the conservatively modified peptide is:

```
    X- SWETWEREIENYTRQIYRILEESQEQQDRNERDLLE -Z,
```

"X" may represent an amino group, a hydrophobic group, including but not limited to carbobenzoxyl, dansyl, or tert-butyloxycarbonyl; an acetyl group; 9-fluorenylmethoxy-carbonyl (FMOC) group; a macromolecular carrier group including but not limited to lipid fatty acid conjugates, polyethylene glycol, or carbohydrates. "Z" may represent a carboxyl group; an amido group; a tert-butyloxycarbonyl group; a macromolecular carrier group including but not limited to lipidfatty acid conjugates, polyethylene glycol, or carbohydrates.

In one embodiment, the peptide is: $CH_3CO$-SWETW-EREIENYTRQIYRILEESQEQQDRNERDLLE-$NH_2$ (called FS-01 herein after).

In addition, the present invention also provides segments of the antiviral peptide (SEQ ID NO: 1) that shows an antiviral activity. These truncated antiviral peptides can contain 4-36 amino acids (namely ranging from tetrapeptide to 36-amino-acid peptide).

In addition to the whole sequence of the antiviral peptide (SEQ ID NO: 1) and the truncated antiviral peptide, the composition of the present invention can also include peptides comprising SEQ ID NO: 1, or peptides with substitution, insertion, and/or deletion of one or more amino acids in the sequence of SEQ ID NO: 1. The aforementioned peptide comprising SEQ ID NO: 1 can be produced by adding 2-15 amino acid on the terminal of the SEQ ID NO: 1. The amino acid insertion can be made up of a single amino acid residue or a residue segment of 2-15 amino acids. According to an embodiment of the present invention, the amino acid substitutes have protective properties. The protective amino acid substitutes comprise of amino acids with similar charges, sizes, and/or hydrophobic characteristics to the amino acids (one or more) they replace in the peptide. The aforementioned amino acid can be D-isomer or L-isomer amino acid residue, also can be natural or non-naturally occurring amino acid residue.

The pharmaceutical composition of the present invention contains an effective amount of antiviral peptide, the content of the antiviral peptide range from 1 to 100 mg, preferred range is 3-90 mg, 5-80 mg, 7-70 mg, 9-60 mg, 10-50 mg, 15-20 mg, 1-15 mg, 5-15 mg, 20-25 mg, 25-30 mg, 25-100 mg, 30-90 mg, 35-80 mg, 40-70 mg, 45-60 mg, 3 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg or 100 mg. According to a preferred embodiment, the composition contains 20 mg of antiviral peptide.

The pharmaceutical composition of present invention contains 20%-90% (w/w) of antiviral peptide. According to one embodiment, it contains 20% (w/w) of antiviral peptide. According to another embodiment, the composition contains 40% (w/w) of antiviral peptide. According to another embodiment, the composition contains 60% (w/w) of antiviral peptide.

The pharmaceutical composition of present invention can be prepare by any routine method, and be administered through injection, oral, mucosa, rectal and transdermal. It will be detail introduced in the part of "Pharmaceutical Formulation and Administration Route"

The present invention is also directed to a method for preparing a pharmaceutical composition, the method comprising adding to the composition a peptide comprising the amino acid sequence of SWETWEREIENYTRQIYRI-LEESQEQQDRNERDLLE (SEQ ID NO:1), or a conservatively modified variant thereof. In one embodiment, the content of aforementioned peptide range from 1 mg to 100 mg. In another embodiment, the content of the peptide is range from 20% to 90%. In yet another embodiment, the aforementioned method included addition of other antiviral agents into the composition. In one embodiment, the another antiviral agent is selected from reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, γ-interferon, and other anti-HIV agents.

The aforementioned pharmaceutical composition of present invention can be used to prevent or treat HIV infection, to decrease viral load of patient, to increase $CD_4^+$ cell count of HIV patient. Therefore, the present invention also provide a use of the pharmaceutical composition to prepare the drug which is to prevent or treat HIV infection by decrease patient's viral load and increase $CD_4^+$ cell count of HIV patient. According to one embodiment, the viral load effectively decreases by 0.5 log. According to another embodiment, the viral load decrease by 0.7 log. According to another embodiment, the decrease is more than 2 log. According to one embodiment, $CD_4^+$ cell count increases to more than 200 cells/mm$^3$ in patient. According to another embodiment, the cell count is more than 350 cells/mm$^3$. According to another embodiment, the cell count is more than 500 cells/mm$^3$. According to one embodiment, the pharmaceutical composition is used in early stage HIV patient. According to a preferred embodiment, the viral load is no more than 30,000 c/ml in early stage patient. According to another preferred embodiment, viral load is no more than 20,000 c/ml, more preferred viral load is no more than 10,000 c/ml. According to another embodiment, the pharmaceutical composition is given to the patient receiving other antiviral therapeutic agents and the viral load is controlled under 30,000 c/ml, according to a preferred embodiment, the viral load is controlled under 20,000 c/ml, more preferred viral load is controlled under 10,000 c/ml.

The present invention also provides a method for preventing or treating HIV infection, including administering the aforementioned pharmaceutical composition contains 1-100 mg of antiviral peptide with the amino acid sequence of SEQ ID NO:1. According to one embodiment, the pharmaceutical composition contains antiviral peptide ranging within 3-90 mg, 5-80 mg, 7-70 mg, 9-60 mg, 10-50 mg, 15-20 mg, 1-15 mg, 5-15 mg, 20-25 mg, 25-30 mg, 25-100 mg, 30-90 mg, 35-80 mg, 40-70 mg, 45-60 mg, 3 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg or 100 mg. In a preferred embodiment the pharmaceutical composition contains 20 mg of antiviral peptide.

In one embodiment of the present invention, the pharmaceutical composition is given to patient at intervals of once daily, every two days, every three days, every four days, every five days, every six days or every seven days. In a preferred embodiment, the aforementioned pharmaceutical composition is given once daily or once every seven days.

According to one embodiment of the present invention, after given an effective amount of aforementioned composition the maximum plasma concentration of antiviral peptide is 1-250 nM. According to one preferred embodiment, maximum plasma concentration of 5-250 nM, 10-220 nM, 25-200 nM, 30-180 nM, 35-160 nM, 40-140 nM, 45-120 nM, 50-100 nM, 60-90 nM, 70-80 nM, 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 220 nM, 250 nM of antiviral peptide is obtained after given an effective amount of aforementioned composition.

According to another embodiment of the present invention, the patient received treatment is early stage HIV patient. According to a preferred embodiment, the viral load of the patient is no more than 30,000 c/ml. preferred viral load is no more than 20,000 c/ml, more preferred viral load is no more than 10,000 c/ml.

According to another embodiment of the present invention, the HIV patient received treatment is that who is under treatment of other antiviral therapeutic agents and the viral load is controlled within 30,000 c/ml, preferred viral load is no more than 20,000 c/ml, more preferred viral load is no more than 10,000 c/ml.

HIV patient is treated by giving aforementioned pharmaceutical composition according to the method of the present invention, the viral load of the patient can be decreased. The viral load can drop by 0.5 log. According to a preferred embodiment, the viral load decrease by at least 0.7 log. According to another preferred embodiment, the decrease is more than 1 log. According to a more preferred embodiment, the decrease is more than 2 log. Besides, using the aforementioned pharmaceutical composition can increase CD4+ cell count of HIV patient. According to an embodiment, the $CD_4^+$ cell count increases to more than 200 cells/mm$^3$. According to a preferred embodiment, the $CD_4^+$ cell count is to more than 350 cells/mm$^3$. According to another preferred embodiment, the $CD_4^+$ cell count is more than 500 cells/mm$^3$.

The antiviral peptide comprising the amino sequence of SEQ ID NO:1 can be jointly administered with other antiviral agents to achieve better therapeutic outcome, such as synergistic action or decreasing the side effect.

Therefore, the present invention also provide a pharmaceutical composition contains antiviral peptide with the amino acid sequence of SEQ ID NO:1 and other antiviral agents, the use of the pharmaceutical composition to prepare the drug for prevention or treatment HIV infection which can decrease viral load and increase $CD_4^+$ cell count in HIV patient, the method of simultaneously, sequential or by turn administering the antiviral peptide with the amino acid sequence of SEQ ID NO:1 and other antiviral agents to prevent or treat HIV infection. In one embodiment, the another antiviral agent is selected from reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, γ-interferon, and other anti-HIV agents.

The antiviral peptide and some expressions in the present invention are defined hereinafter:

The antiviral peptide in the present invention includes an amino acid sequence of SEQ ID NO:1 (called FS-01 herein after) or conservatively modified variants thereof:

SWETWEREIENYTRQIYRILEESQEQQDRNERDLLE (SEQ ID NO: 1)

As used herein, the single-letter codes represent amino acid residues in common sense in the art as follows:
A=Alanine, R=Arginine, N=Asparagines, D=Aspartic acid, C=Cysteine, Q=Glutamine, E=Glutamic acid, G=Glycine, H=Histidine, I=Isoleucine, L=Leucine, K=Lysine, M=Methionine, F=Phenylalanine, P=Proline, S=Serine, T=Threonine, W=Tryptophan, Y=Tyrosine, V=Valine.

The antiviral peptide in present invention can be manufactured by common techniques and methods known in the art. For instance, being synthesized on a certain solid or in solution, produced by recombinant DNA technology, or synthesized as several separated segments and then connected together.

As used herein, "conservatively modified" refers to structurally modify the amino acid sequence without substantially affecting the activity of the peptide, using techniques such as amino acid substitution, terminal modification (e.g., introduction of an acyl group, hydrophobic group or macromolecular carrier group etc. at one or two terminals). The conservatively modified peptide should retain at least 60% of the activity of the original peptide, preferred is at least 80%, more preferred is 90% of the activity of the original peptide.

As used herein, "viral infection" refers to a morbid state in which the virus invades a cell. When the virus enters a healthy cell, it utilizes the host reproduction mechanism to replicate itself, which finally kills the cell. After budding from the cell, those newly produced progeny viruses continue to infect other cells. Some viral genes can also integrate into host chromosome DNA in the form of provirus, and it is called as latent infection. The provirus reproduces itself with the replication of the host chromosome, and can bring the infected people into morbidity at any moment if activated by various factors inside or outside the body.

As used herein, "prevent or treat HIV infection" refers to suppressing the replication and the spread of viruses, preventing the virus self-settling inside the host, and improving or alleviating the symptoms caused by viral infection. The criteria for effective therapy include lower viral load, immune reconstruction, lower mortality rate, and/or morbidity rate, etc.

As used herein, "derivatives" refers to any peptides contain the sequence of the antiviral peptide, homolog, analog, or segment of the antiviral peptide, or peptides that have substitute, insertion, and/or deletion of one or more amino acids.

As used herein, "therapeutic agent" refers to any molecule, compound, or drug conductive to the treatment of viral infection or virus-caused diseases, especially antiviral agents.

As used herein, "synergic action" refers to a joint drug administration that is more effective than the additive action of merely using any of two or more therapeutics to cure or to prevent viral infection. The synergic effect can increase the efficacy of antiviral drugs and avoid or alleviate viral tolerance against any single medicine.

The Progress of HIV Infection

It is commonly known that after the body is infected by HIV, the progress of the disease depends on two factors— virus and body immunity. On one hand, plasma viral load directly indicates virus replication in host body. On the other hand, number of CD4+ cell, the most important immune cell, indicates the degree of damage to the body immune system.

T lymphocytes are a group of most important function cells in immune system, mainly composed of CD4+ and CD8+ cell subgroups which keep normal immune function of the body by interacting and balancing. When quantity or function abnormality occurs in lymphocyte subgroup, the immune system will be functional disorder and series of pathological changes are developed (Domestic technological specification for AIDS assay, 2004. Chinese Center for Disease Control and Prevention).

1) Decrease of $CD_4^+$ Cell Count

After HIV infection, $CD_4^+$ cells decrease continuingly. The period of acute infection is featured by temporal fast drop of $CD_4^+$ cell in short term. Number of $CD_4^+$ cells is capable of recovering to normal or close to normal level without special treatment in most infection. The period of asymptomatic infection is featured by continuing chronically decrease of $CD_4^+$ cells whose number mostly ranges between 800-350 cells/mm$^3$, duration of this period fairly varies (from several months to tens of years), lasts for approximately eight years on average. After entering the period of symptomatic infection, $CD_4^+$ cells decrease dramatically again, the number of $CD_4^+$ cells is no more than 350 cells/mm$^3$ in most infected people. $CD_4^+$ cells number drops fast to below 200 cells/mm$^3$ in some late stage patients.

Decrease of $CD_4^+$ cell number results from many factors, it may because increasing damage of $CD_4^+$ cells; reducing generation of $CD_4^+$ cells; retaining of peripheral $CD_4^+$ cells in lymphoid tissue, et al. In the progress of the disease, the immune system is unable to respond normally to specific antigens because of the loss of antigen-specific T cell clones (Sean Emery, et. al. Immune reconstruction in HIV infection. *Current Opinion in immunology.* 9:568-572 (1997)), which results in development of various opportunistic infections and tumors.

2) Dysfunction of $CD_4^+$ Cell

This is manifested by replacement of T helper cell 2 (Th2) by T helper cell 1 (Th1), functional damage of antigen presenting cells, reduction of IL-2 and lost the capability of antigen-reactive response, which leads to various infections in HIV-positives or AIDS patients.

3) Abnormal Immunological Activation

Another immunopathogenesis change is exceptional immune activation after HIV infection. Expression of the activation markers in $CD_4^+$ and $CD_8^+$ lymphocytes abnormal increases, such as CD69, CD38 and HLA-DR, which is well correlated with HIV plasma viral load. In the progress of disease, cell activation continuously increases. Thus, the state of abnormal immune activation can be utilized to evaluate the change of viral load, to predict the speed of the depletion of $CD_4^+$ cells (Guideline for diagnosis and treatment of AIDS. Chinese Medical Association, 2005).

Important Indicator in HIV Treatment

Viral load resulted from the co-contribution of virus replication and immune clearance to virus, reflects concentration of virus in plasma, is an important indicator to identify the progress of disease (Yao, Jun et al. Virological and immunological study of HIV-1 infected individuals in different stages of infection [J]. CHINESE *JOURNAL OF AIDS & STD.* 12(1):1-3 (2006)). $CD_4^+$ cell is regarded as another important indicator to identify progress of HIV infection. They can be utilized alone or combined together as important indicators to evaluate disease progression, clinical therapy, therapeutic effect and prognosis.

Commonly used technologies in plasma viral load testing include retroviral PCR (RT-PCR) assay, nucleic acid sequence-based amplification (NASBA) assay and branched DNA (bDNA) assay. The meaning of measuring viral load in clinical practice is to predict disease progress, provide basis for antiviral therapy initiation, evaluate therapeutic effect, direct therapy regimen, and be as diagnosis reference for early stage HIV infection (Guideline for diagnosis and treatment of AIDS. Chinese Medical Association, 2005).

One of classification standards of HIV infection is CD4+ cell number. American Centers for Disease Control and Prevention (CDC) categorizes HIV infection or AIDS patient on the basis of CD4+ cell number, which is commonly used globally. Additional, monitor the change of absolute $CD_4^+$ cell number can help to understand progress of disease in patient, decide appropriate therapeutic regimen, and observe response of patient to treatment, such as judging the clinical complication of HIV infected people—when $CD_4^+$ cell number is less than 200 cells/mm$^3$, risk of infection by Pneumocystis carinii pneumonia increases; when $CD_4^+$ cell number is less than 50 cells/mm$^3$, risk of infection by Cytomegalovirus (CMV) increases. It can be concluded from $CD_4^+$ cell number that immune state and disease progression, disease classification and therapy initiation, therapeutic effect and clinical complication in HIV infected people. Therefore, it is recommended to periodically monitor $CD_4^+$ cell in 111V infected people and AIDS patients.

Progression of HIV Infection

It is a long and complicated process from primary HIV infection to end-stage. In different stages, clinical manifestation is diverse, usually divided into three stages—acute HIV infection, asymptomatic infection and AIDS.

Acute HIV infection usually occurs 2-4 weeks after primary infection. Some infected people develop clinical symptoms caused by HIV viremia and acute injury of immune system.

An HIV patient can enter the asymptomatic infection stage from acute HIV infection with or without obvious clinical symptoms. This period may last for 6-8 years and the duration depends on quantity of virus, sex, route of infection, individual diversity in immune condition, nutrition state, life style and other factors. In the stage of asymptomatic infection, immune system damages, $CD_4^+$ cell number drops, and it is infectious meantime, which result from continuous replication of HIV in patient. Relationship between viral load and six-year morbidity is: morbidity rate is 5.4% when viral load is less than 500 c/ml; morbidity rate is 16.6% when viral load ranges from 500 to 3,000 c/ml; morbidity is 31.7% when viral load ranges from 3,001 to 10,000 c/ml; morbidity is 55.2% when viral load ranges from 10,001 to 30,000 c/ml; morbidity is 80% when viral load is more than 30,000 c/ml.

When $CD_4^+$ cell number is less than 200 cells/mm$^3$, relationship between viral load and risk of developing into AIDS in 3~6 months is: when viral load is less than 10,000 c/ml, the risk is 4.9%; when viral load ranges from 10,000 to 29,999 c/ml, the risk is 12.7%; when viral load ranges from 30,000 to 99,990 c/ml, the risk is 17.7%; when viral load is more than 100,000 c/ml, the risk is 22.4%. Under the condition of equal $CD_4^+$ cell number, it is more risky for elder people to develop into AIDS than for younger people (Domestic technological specification for AIDS assay, 2004. Chinese Center for Disease Control and Prevention).

Under different conditions of CD4+ cell number—less than 200 cells/mm$^3$, ranging from 200 to 350 cells/mm$^3$, or more than 350 cells/mm$^3$, evaluation of disease progression was performed in people 3-year or 9-year later from HIV infection with viral load less than 10,000 c/ml, ranging from 10,000 to 30,000 c/ml, or more than 30,000 c/ml. The overall trend is the lower $CD_4^+$ cell number is, the higher viral load is, the longer infection lasts, and the higher AIDS morbidity rate is. For an example, when viral load was more than 30,000 c/ml, AIDS morbidity rate of 3-year or 9-year after HIV infection in those with $CD_4^+$ cell number less than 200 cells/mm$^3$ are 86% and 100%; for those with viral load more than 350 cells/mm$^3$, the morbidity rates are 40% and 85% respectively (Mellors J W, Rinaldo C R, Gupta P, et al. Prognosis in HIV-1 infection predicted by the quantity of virus in plasma. Science. 272 (5265):1167-70 (1996)).

The end stage of HIV infection is AIDS. Plasma HIV viral load increases obviously, $CD_4^+$ cell number in patient drops dramatically, mostly to less than 200 cells/mm$^3$. The clinical manifestations in this stage include HIV related symptoms, various opportunistic infections and tumors (Guideline for diagnosis and treatment of AIDS, Chinese Medical Association, 2005).

Classification of HIV infection varies slightly in different organizations. American CDC classifies HIV infection into 9 categories according to $CD_4^+$ cell number and clinical symptoms. The ranges of $CD_4^+$ cell number are—more than 500 cells/mm$^3$, 200-499 cells/mm$^3$, and no more than 200 cells/mm$^3$. In these three ranges, they are further divided into three stages—acute HIV infection (Category A), asymptomatic HIV infection (Category B) and AIDS-defining illness (Category C). HIV infected people with $CD_4^+$ cell number less than 200 cells/mm$^3$ or those included in Category C all belong to AIDS patient. In 2006, United States Department of Health and Human Services (DHHS) published three conditions to receive HIV therapy including clinical symptoms, $CD_4^+$ cell number and viral load. Antiretroviral therapy is recommended for all patients with an AIDS-defining illness, or severe symptoms of HIV infection, or those with CD4$^+$ cell number less than 200 cells/mm$^3$ which is defined as Category AI; There is no specific conclusion on whether to initiate treatment in asymptomatic infected people with $CD_4^+$ cell number more than 350 cells/mm$^3$ and viral load more than 100,000 c/ml who belong to Category CII. Deferred therapy is recommended to those belong to Category DII with $CD_4^+$ cell number more than 350 cells/mm$^3$ and viral load less than 100,000 c/ml. The International AIDS Society (IAS) recommends starting treatment in HIV infected people with viral load more than 30,000 c/ml and $CD_4^+$ cell number less than 350 cells/mm$^3$; deferring treatment in those with viral load less than 5000 c/ml and $CD_4^+$ cell number more than 500 cells/mm$^3$ (Domestic technological specification for AIDS assay, 2004, Chinese Center for Disease Control and Prevention). Chinese CDC suggests a better effect of antiviral therapy comes out if treatment starts when viral load has obtained a specific level (e.g. more than 35,000-50,000 c/ml) (Domestic technological specification for AIDS assay, 2004, Chinese Center for Disease Control and Prevention). Chinese Medical Association recommends starting treatment for acute HIV infection regardless of $CD_4^+$ cell number; in stage of asymptomatic infection, $CD_4^+$ cell number ranges from 200 to 350 cells/mm$^3$, treatment should start when following conditions occurs: 1) $CD_4^+$ cell number decreases more than 30% within one year; 2) viral load is more than 100,000 c/ml; 3) patient urgent requires for treatment and ensures well compliance.

When to initiate treatment also varies according to different organizations, it is commonly known that the higher viral load is, the lower $CD_4^+$ cell number is, the stronger recommendation of starting treatment is. However, considering to fairly high $CD_4^+$ cell number, e.g. more than 350 cells/mm$^3$, or low viral load, e.g. less than 5000 c/ml, treatment is recommended to defer. It is because many influence factors should be considered at this time, e.g. $CD_4^+$ cell number, baseline viral load, patient's compliance, side-effects and long-term toxicity of the drug, and cost of the therapy, et al. (Guidelines for the use of Antiretroviral Agents in HIV-1-Infected Adults and Adolescents. aidsinfor.nih.gov. 2006). According to an embodiment in the present invention, there were differences in antiviral effect when using the inventive pharmaceutical composition in patients with different baseline viral loads. Antiviral effect appeared better when viral load had been relatively low. For example, when viral load was less than 10,000 c/ml, the load dropped by more than 1 log in value after two-week successive administration of the inventive composition and would further drop with extension of treatment. This suggested, at least in that embodiment, that better antiviral effect may be obtained by administration of the inventive pharmaceutical composition in patient with early stage HIV infection or when viral load has been under control by other antiviral therapeutics.

Therapeutic Efficacy of HIV Infection

It is commonly considered that whether a therapy is effective or not can be judged by monitoring viral load. If viral load drops more than 0.5 log after treatment in comparison with baseline, then the therapy is regarded as effective (Domestic technological specification for AIDS assay, 2004, Chinese Center for Disease Control and Prevention). For those with plasma viral load ranging from 10,000 c/ml to 30,000 c/ml and $CD_4^+$ cell number less than 350-500 cells/mm$^3$, viral load should drop 1-2 log after 4-8 weeks treatment, and then achieve undetectable viral load (<50 c/ml) after 16-24 weeks (Kievits T, Can Gemen B, et al. NASBA isothermal enzymatic in vitro nucleic acid amplification optimized for the diagnosis of HIV-1 infection, *J Virol Methods*, 35:273-86 (1991)). Mellors et al. (Mellors J W, MunozA, Giorgi J V, et al. Plasma viral load and CD4+ lymphocytes as prognostic markers of HIV-1 infection. *Ann Intern Med.* 126:946-54 (1997)) found that if viral load drops 0.5 log, the clinical risk decreases 30%; if $CD_4^+$ cell number improves 10%, the risk decreases 15%.

After antiviral treatment, viral replication is suppressed, peripheral $CD_4^+$ cell number increases which is indicated by two phases: in the first 8-12 weeks after treatment, lymphocytes retained in lymphoid tissue because of inflammation redistribute which leads to increase of peripheral lymphocytes including $CD_4^+$ cell. In the first week after infection, $CD_4^+$ cells show an increase in memory cell CD45 RO$^+$. Several weeks later, naïve T cell CD45 RA$^+$ develops. During second stage, increase of $CD_4^+$ cell slows down, CD45 RA$^+$ 62L$^+$ phenotypic naive $CD_4^+$ cells develop (Christoph G. et. al. Immune reconstitution with antiretroviral therapies in chronic HIV-1 infection Journal of Antimicrobial Chemotherapy [J]. *JAC,* 2003, 51: 1-4). Expression of CD28, which is an activation helper molecule, increases; immunoactivation marker CD38 on surfaces of $CD_4^+$ and $CD_8^+$ cells decreases (Sean Emery, et. al. Immune reconstitution in HIV infection *Current Opinion in immunology.* 9: 568-572 (1997)).

In addition to achieve undetectable viral load, the goal of antiviral treatment is also to restore immune system which is able to control viral load in return. It is especially important for those who have used many kinds of antiviral agents, but still unable to achieve undetectable viral load. It is impossible for them to suppress the disease by adding more drugs in regimens. Therefore, main goal for treatment is to partially inhibit viral replication and to recover immune function (www.aidsmap.com).

Immune reconstruction in AIDS patient is defined as abnormal immunological change caused by HIV can restore to normal or close to normal: 1) recovery of decreased $CD_4^+$ cells; 2) regain the capability of $CD_4^+$ cell to normal reaction against memory antigenic stimulation; 3) recovery of the abnormal immune activation in patient. Of course, immune reconstruction also includes decrease incidence of AIDS-related opportunistic infections and tumors, decrease mortality and morbidity of AIDS after antiviral treatment. However, antiviral therapy has its limitation on immune reconstruction for AIDS: 1) unable to reconstruct immune function in all AIDS patients; 2) $CD_4^+$ cell antigenic stimulation reaction against HIV is unavailable, $CD_8^+$ cell antigenic stimulation reaction against HIV also decreases, which means patients must using medicines for long term (Guideline for diagnosis and treatment of AIDS. Chinese Medical Association, 2005).

In the present invention, early stage HIV patient is defined from three aspects, including infection duration, viral load and $CD_4^+$ cell count. Early stage HIV patient is the patient who is within 15 years from diagnosis of HIV infection, further clarifying, is within 10 years from diagnosis of infection, or within 3 to 9 years, or within 5 to 8 years. From the aspect of viral load, early stage HIV patient is those with viral load less than 30,000 c/ml, further clarifying, viral load is less than 20,000 c/ml, according to an embodiment, the viral load is less than 10,000 c/ml. Early stage HIV patient is also defined as those with $CD_4^+$ cell count ranging from 200 to 500 cells/mm$^3$, further clarifying, is those with $CD_4^+$ cell count ranging from 350 to 500 cells/mm$^3$.

Administration Dose

In the treatment of acute viral infection in mammals such as human, antiviral peptide or its derivatives should be administered in effective amount sufficient to suppress viral replication. This effective dose can be determined by methods generally known to one of skill in the art, including setting parameters such as biological half-life period, bioavailability and toxicity, etc.

The dose of drug depends upon the plasma concentration of the antiviral peptide which is to relief the symptoms or to extend survival time of the patient. It can be determined trough cell culture assay or animal studies according to standard pharmaceutical procedure. According to an embodiment, FS-01 was administrated subcutaneously or intravenously to rhesus monkeys, the half-life ($T_{1/2}$) is 8.13±3.1 h, bioavailability (BA) is 50%, time to achieve peak plasma concentration ($T_{max}$) is 0.25 h~2 h, peak plasma concentration ($C_{max}$) is 508.17±167.30 ng/ml (107.5±35.4 nM), plasma concentration at 24 h ($C_{24}$) is more than 9.8 ng/ml (2.07 nM).

It is more precise to get data from human trials. Virus replication, especially HIV concentration, is able to suppressed by an effective amount of antiviral peptide in plasma, by administration the effective amount of pharmaceutical acceptable antiviral peptide every time, such as administration of 1-100 mg antiviral peptide, preferred dose of 3-90 mg, 5-80 mg, 7-70 mg, 9-60 mg, 10-50 mg, 15-20 mg, 1-15 mg, 5-15 mg, 20-25 mg, 25-30 mg, 25-100 mg, 30-90 mg, 35-80 mg, 40-70 mg, 45-60 mg, 3 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg or 100 mg of antiviral peptide. According to an embodiment, the pharmaceutical composition containing the antiviral peptide was given to HIV patients at different doses, it can effectively decrease the HIV viral load in plasma and increase $CD_4^+$ cell count, and the effect is shown in fairly low dose, such as 5 mg group.

In joint administration with antiviral peptide or its derivatives, the effective doses of the therapeutic agents (such as antiviral agents) depend on the recommended doses well-known to one skill in the art. The preferred dose for joint administration is about 10-50% lower than the recommended dose for separate administration in literature. Medical professionals should pay attention to the dose when toxic reactions occur. The doctor should know how and when to suspend or terminate the administration and to regulate the dose to a lower level when marrow inadequacy, liver and/or kidney inadequacy, or serious drug interactions occurs. In contrast, if the anticipated clinical therapeutic efficacy is not achieved, the doctor should also know how to enhance the dose.

Dose Interval

Dosing intervals to prevent or treat viral infection depend on the speed of absorption, deactivation, excretion of the drug, and other factors well-known to one skill in the art. It should be noted that dosage should be adjusted according to relief of the disease. Specific regimen should be individualizing administered and supervised, and the administration should adjust according to duration of treatment according to professionals. Dosage provided in the present invention is taken as an example, but not a limit to the range or practice of the pharmaceutical composition. The active component can be administered once, or subdivided into smaller doses according to diverse intervals.

According to one embodiment, healthy volunteers received single injection of pharmaceutical composition containing 10 mg, 20 mg, and 30 mg of FS-01. Maximum concentration of antiviral peptide in plasma is 104±62 ng/ml (22.0±13.1 nM), 213±62 ng/ml (45.1±13.1 nM) and 250±197 ng/ml (52.9±41.7 nM), respectively. The plasma drug concentration 72 hours after dosing is approaching baseline. So dose interval can be inferred according to the method well-known in the art, to sustain the drug concentration above the effective amount to inhibit virus replication, such as twice daily, once daily to several days. According to an embodiment, the prior amount of antiviral peptide is administered every two days, three days, four days, five days, six days, seven days or longer intervals.

HIV infection can be prevented or treated by the administration of different doses of antiviral peptide or different dose intervals, to maintain the effective concentration enough for suppressing the virus replication. According to one embodiment the concentration ranges from 1 to 250 nM. In a preferred embodiment the concentration of antiviral peptide is 5-250 nM, 10-220 nM, 25-200 nM, 30-180 nM, 35-160 nM, 40-140 nM, 45-120 nM, 50-100 nM, 60-90 nM, 70-80 nM, 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 220 nM, 250 nM.

Pharmaceutical Formulation and Administration Route

The best method of giving the present antiviral peptide including (but not limited to): injection (such as intravenous, intraperitoneal, intramuscular, and hypodermal injection, etc.); epithelium or mucosa absorption, such as actinal mucosa, rectal, vaginal epithelium, pharynx nasalis mucosa, enteric mucosa, etc; per os; transdermal or other pharmacologically feasible administration routes. In order to prevent or treat viral infection, patients are administrated directly with the antiviral peptide or drug composition containing the antiviral peptide to obtain the dosage amount for treating viral infection. The preparation and administration technology for this application is well-known to one of skill in the art.

The present invention also includes the use of pharmacologically acceptable carrier to prepare a proper dosage formulation of the antiviral peptide and/or pharmaceutical composition for different administration route.

Injection is a sterilized or aseptic pharmaceutical formulation used for administration, divided into four types: solution, suspension, emulsion, and aseptic powder (powder injection). It is one of the most popular formulations, having many advantages—quick action, reliable, fit for drugs unmeet oral administration, fit for patient unable to take medicine orally, may target local area. However, there are some drawbacks—inconvenient to use, pain during injection, and complicated manufacture process. Administration route depends on medical need, including intravenous injection, intraspinal injection, intramuscular injection, subcutaneous injection and intradermal injection.

Sterilized powder formulation for injection is simply called powder injection. For those medicine unstable in aqueous solution, for example, penicillin G, cephalosporins, and biologics such as medical enzymes (trypase, coenzyme A) and blood plasma, have to be prepared into sterilized powder for injection. According to various conditions of manufacture and to different features of drugs, the powder got through lyopyilization is usually called lyophilized injection powder, and through other ways, such as crystallization in sterilized solvent or spray drying, is usually called sterilized subpackage for injection.

Freeze drying is an arescent method. It needs to pre-freeze the solution containing the drug into solid, the water sublimates from solid to gas without going through liquid state at low atmosphere and low temperature. This can be adopted by the drugs unstable in aqueous solution or to heat. Advantages of freeze drying include—avoid decomposition or degeneration of the drug, e.g. protein in product will not denaturalize; make product more loosened which could re-solve quickly to recover the solution features of the original drug; low moisture which ranges in 1~3%; meanwhile, the drying is performed in vacuo, so it is unlikely to oxidated which contributes to longer shelf-life; less particle substances in the product compared with other methods because of fewer contamination incidence; accurate dosage and better appearance.

To guarantee the drug powder meet the quality requirements of injection, it should be firstly tested that the stability of the substance to heat, critical relative humidity, crystal form, bulk density (specific volume) and other physicochemical properties. The drug powder in accordance to the requirements for injection is subdivided into clean sterilized vials or ampoules under the condition of aseptic operation, sealed up as a convenient dosage form for clinical use. The dosage form prepared by freeze drying is called freeze-dried powder injection.

Besides the active ingredient, supplemental substances are added into the injection to improve the efficacy, safety and stability of the injection during preparation. Commonly used supplemental substances are solubilizing agent, buffer, suspending agent, stabilizer, chelator, oxidation inhibitor, bacteriostatic, local anesthesia agent, isoosmotic adjusting agent, loading agent, protectant et al., for example, acetate, phosphate, carbonate, glycine, mannitol, lactose and human serum albumin. The preparation of drug can be performed by methods generally known to one of skill in the art—antiviral peptide can be prepared into asepsis aqueous solution without pyretogen, the solution can be distilled water, preference is saline water, phosphate buffered saline or 5% glucose solution. Selectively adjust the pH value to physiological acceptable, such as to subacidity or physiological pH value, then after sterilization or aseptic filtration, then transfer the solution to a unit container, e.g. a vial, and then freeze dry into a convenient dosage unit for use. How-to-use of the drug should be noted on the inner/outer package of the dosage form, such as the weight or content of the active ingredient and administration interval. According to one embodiment, the composition is subcutaneously administered once a day; according to an alternative embodiment, the composition is subcutaneously administered every seven days. The pharmaceutical dosage unit is redissolved in aseptic water before administration. According to an alternative embodiment, the different doses of proper powder injections containing the antiviral peptide were prepared by utilizing different kinds of pH regulator, e.g. phosphate and carbonate.

The antiviral peptides of the present invention can also be prepared as a solution fit for oral administration by use of a pharmacologically acceptable carrier well-known in the art. Appropriate carriers are necessary for preparing the peptides or combinations into tablets, pills, capsules, liquid, gel, syrups, slurry, suspensions, and other dosage formulations.

The antiviral peptides of the present invention can be administered by routes including actinal, rectal, dialysis membrane, or enteric administration; extragastrointestinal administration including intramuscular, hypodermal, intramedullary, introthecal, directly intraventricular, intravenous, intraperitoneal, intranasal, or intraocular injection; percutaneous, local, vaginal administration, etc. The dosage formulations include (but not limited to) tables, pastille, powders, suspensions, suppositories, solution, capsules, frost, plasters, and micro-motors.

The oral dosage formulation of the antiviral drug compositions of the present invention can be ground together with solid excipients into a well-distributed mixture and then processed into granules that are further processed into tablets or the kernel of sugar-coated tablets; if necessary, proper adjuvant can be added to the mixture. Proper excipients and fillers can be sugar, such as lactose, saccharose, mannitol, or sorbicolan; fibrin products, such as cornstarch, wheaten starch, rice starch, potato starch, glutin, tragacanth, methyl cellulose, hydroxypropylmethyl cellulose, sodium carboxymethyl cellulose, and/or polyvinylpyrrolidone. If necessary, disintegrants, such as cross-linked polyvinylpyrrolidone, agar, alginic acid, or its salt-like alginate sodium. Proper coat should be provided to the kernel of sugar-coated tablets. The coat can be made from concentrated sugar solution containing Arabic gum, talcum, polyvinylpyrrolidone, carbopol gel, polyethylene glycol, titanium oxide, cellulose nitrate, and proper organic solvent or solvent combination. Different combinations of coloring matter or edible pigment can be added to the tablets or coat of sugar-coated tablets to discriminate or designate the active compound.

The drug composition for oral administration includes the stuffing-type capsule and the sealed soft capsule made of glutin and a plasticizer such as glycerin or sorbic acid. The stuffing-type capsule contains a filler, such as lactose, an adhesive, such as starch, and/or a lubricant, such as talcum or stearate. In addition, a stabilizer can also be used to stabilize the active components. In the soft capsule, the active compound can be dissolved or suspended in some proper liquid, such as fatty oil, liquid olefin, or liquid-like polyethylene glycol. Besides, a stabilizer can also be added. All the dosage formulations for oral administration should be convenient for patients. In the case of actinal administration, the above mentioned combination can be prepared into the convenient dosage formulations of troche.

In the case of inhalation administration, the antiviral peptides or compositions of the present invention can be readily released in the form of aerosol by use of high-pressure package or atomizer, or by use of some proper propellant such as dichlorodifluoromethane, trichlorofluoromethane, dichlorotetrafluoroethane, carbon dioxide or other proper gases. In the case of high-pressure aerosol, the dosage unit can be defined by the quantity of measured release with one valve. The glutin capsule and cartridge used as insufflator or exsufflator can be produced as a mixture containing the antiviral peptides and a proper pulverous substrate (such as lactose or starch).

The antiviral peptides or compositions of the present invention can be prepared into a dosage formulation for extragastrointestinal administration. For example, they can be prepared into a formulation for injections that include cluster-drug injection or continuous intravenous infusion. The preparation for injection can be packed in the form of unit dosage. For example, it can be packed into ampoules. Preparations in large dosage can also be packed in the form of unit dosage, such as ampoule or large-dosage container, and added with preservative. The combinations of the present invention can take the form of suspension, solution or emulsion with oil or water as its medium, and can contain some additives, such as a suspending agent, stabilizer, and/or dispersant.

The drug compositions for extragastrointestinal administration can be in a water solution of the active substance, namely the water-dissolved form. The suspension of the active substance can also be produced as a proper oil-like suspension injection. The proper oleophilic solvent or vector includes fatty oil such as gingeli oil, or synthesized fatty acid ester such as ethyl oleate or triglyceride, or liposome. Water-like suspension for injection can contain substance that increases the suspension viscosity, such as sodium carboxymethyl cellulose, sorbic alcohol, and glucosan. The above mentioned suspension can also contain selectively a proper stabilizer or substance that increases the compound solubility in order to prepare a high-concentration solution. The active component of the pulverous injection can be dissolved in some proper solvent, such as sterile water for injection that is in the absence of pyretogen, before administration.

The antiviral peptides or compositions of the present invention can also be prepared into rectal dosage formulations such as suppositories or retained enemas. They can be prepared with frequent substrate such as cacao butter or other glyceryl esters.

Apart from the dosage formulations that have been described, the antiviral peptides or drug compositions can also be prepared as long-acting dosage formulations that can be administered by hypodermal or intramuscular planting or intramuscular injection. Therefore, the peptides and its derivatives or drug combinations can be prepared with proper polymers, hydrophobes (oil emulsion, for example), ion exchange chromatography, or hardly soluble derivatives, such as hardly soluble salt.

The drug carriers for hydrophobic peptides of the present invention are a co-dissolved system of organic polymers and aqueous phase that blends with water and contains benzyl alcohol and non-polar surfactant. This co-dissolved system can be a VPD co-dissolved system. VPD is a solution containing 3% (W/V) benzyl alcohol, 8% (W/V) non-polar surfactant multiethoxyaether and 65% (W/V) polyethylene glycol 300 in absolute alcohol, while a VPD co-dissolved system (VPD: 5W) is prepared with VPD diluted in water by 1:1 and 5% glucose. This kind of co-dissolved system can dissolve hydrophobes better while it will produce low toxicity in systemic administration. As long as its solubility and toxicity are not changed, the proportions of the co-dissolved system can be altered greatly. In addition, the components of the co-dissolved carrier can also be changed. For example, other non-polar surfactant with low toxicity can be used to substitute for multi-ethoxyaether; the proportion of polyethylene glycol can also be changed; other biologically-blending polymers, such as polyvinylpyrrolidone, can be used to substitute for polyethylene; other sugar or polyose can be used to substitute for glucose.

The antiviral peptide composition can also include proper carrier-like excipients in solid or gel phase. These carriers or excipients include (but not limited to) calcium carbonate, calcium phosphate, various sugar, starch, cellulose derivatives, gelatin, or polymers, such as polyethylene glycol.

The pharmaceutical compositions of the present invention also include the combination of active components in effective dose used to obtain the therapeutic purpose. The method of determining effective dose is well-known to one of skill in the art.

Joint Administration

The present invention also provides a joint administration of antiviral peptide with other agents, such as other antiviral agents, in the treatment and/or prevention of viral infection, especially HIV infection. These agents may or may not have the same sites or mechanisms in action as viral fusion inhibitors. As a result, cooperative or synergistic effects may result from joint drug administration.

The joint drug administration can prevent synplasm formation and HIV replication, and thus suppressing the reproduction of HIV in the patients. The joint administrations of the present invention can also be used to alleviate or cure the diseases associated with HIV infection. For example, antiviral peptide can be administered jointly with antifungal agents, antibiotics, or other antiviral agents to suppress HBV, EBV, CMV infection and other accidental infection (including TB).

The present invention provides an improved antiviral therapy for the treatment of broad viral (including HIV) infection. In addition, the present invention provides a method of joint drug administration aimed at boosting the therapeutic effect, including the use of antiviral peptide, at least a different medicine, and/or a pharmacologically acceptable vector. The combination therapy can prevent the virus from building up a tolerance against each therapeutic alone, and at the same time reduce drug toxicity and enhance the therapeutic index.

According to an embodiment of the present invention, antiviral peptide can be administered with other agents in all the following, including (but not limited to): simultaneous administration, sequential administration, periodic administration, and periodic therapy (for example, administration of an antiviral compound, then a second antiviral compound within a certain period of time, repeating such administration sequence (namely the period) to reduce possible drug resistance of the antiviral therapy).

The present invention also provides a new therapeutic method which can reduce the effective dose and toxicity of other antiviral therapeutic agents. Furthermore, joint administration of drugs can inhibit viral infection of host cells through different mechanisms, which not only increase the antiviral efficacy but also prevent the viruses from develop resistance against any therapy alone. The probability of successful treatment is therefore increased.

The agents used jointly with antiviral peptide include any drugs which are known or under experiment. According to a preferred embodiment of the present invention, the antiviral peptide or its derivatives are administered together with another agent with a different mechanism. These agents include (but not limited to): antiviral agents, such as the cytokines rIFNα, rIFNβ, and rIFNγ; reverse transcriptase inhibitors, such as AZT, 3TC, ddI, ddC, Nevirapine, Atevirapine, Delavirdine, PMEA, PMPA, Loviride, and other dideoxyribonucleosides or fluorodideoxyribonucleoside; viral protease inhibitors, such as Saquinarir, Ritonavir, Indinavir, Nelfinavir, and VX-478; hydroxyurea; viral mRNA capping inhibitors, such as viral ribovirin; amphotericin B; ester bond binding molecule castanospermine with anti-HIV activity; glycoprotein processing inhibitor; glycosidase inhibitors SC-48334 and MDL-28574; virus absorbent; CD4 receptor blocker; chemokine co-receptor inhibitor; neutralizing antibody; integrase inhibitors, and other fusion inhibitors.

It is believed that HIV and other viruses replicate themselves ceaselessly 24 hours a day from the moment of infection. Thus, it is necessary to use antiviral agents at different stages of viral infection. The present invention also provides a joint administration of the peptide with different antiviral agents, to inhibit virus-cell fusion and intercellular spread of viruses.

Therefore, the present invention provides an improved antiviral therapy for the treatment of broad viral (including HIV) infection. In addition, the present invention provides a method of joint drug administration aimed at boosting the therapeutic effect, including the use of the antiviral peptide, its derivatives, at least a different medicine, and/or a pharmacologically acceptable vector. The combination therapy can prevent the virus from building up a tolerance against each therapeutic alone, and at the same time reduce drug toxicity and enhance the therapeutic index.

The present invention provides a therapeutic method for HIV infection of human and other mammals. This method comprises administering antiviral peptide in effective dose as well as at least another agent that is preferably a different antiviral agent.

The present invention provides a method for the treatment of viral infection (especially HIV infection). The present invention also provides a drug combination for the treatment of HIV infection, the combination has an effective dose of antiviral peptide and at least a different antiviral compound. Preferably, antiviral peptide should be used together with retrovirus inhibitors, viral protease inhibitors, cytokines, cytokine inhibitors, or other viral fusion inhibitors. The joint drug administration will be more effective in suppressing viral replication and transmittal.

The methods of the present invention include administration of antiviral peptide alone, and joint drug administration of antiviral peptide with other antiviral agents. Antiviral peptide and at least one of other agents can be administered simultaneously (used as a mixture or separately), or sequentially (including period therapy). The period therapy administers to the patients an antiviral compound during a certain period and then administering a second antiviral compound during another period. Such administration sequence (namely the period) is repeated to alleviate the toxicity, as well as the drug resistance of the therapy.

The present invention also provides a different period therapy that comprises administering the peptide of the present invention first, and then another antiviral agent, and then the peptide of the present invention again or another viral fusion inhibitor. Consequently, the inhibitor of the present invention or its derivative is administered together with other antiviral agents.

The "joint administration" includes not only using two or more therapeutics together as a mixture therapy, but also using two or more therapeutics separately but simultaneously, for example, via different veins into the same body. The "joint administration" also includes administering the drugs sequentially, namely administering one drug and then the second drug.

The preferred antiviral agents used together with antiviral peptide can attack the viruses in the following different modes: inhibiting the reverse transcriptase, inhibiting the capping of viral mRNA, inhibiting HIV protease, inhibiting the glycosylation of proteins, inhibiting integrase, and inhibiting viral fusion. Drugs based on those attacking modes above include (but not limited to): antiviral agents, such as the cytokines, including rIFNα, rIFNβ, and rIFNγ; cytokine inhibitors; reverse transcriptase inhibitors, such as AZT, 3TC, ddI, ddC, d4T, Nevirapine, Atevirapine, Delavi Trdine, PMEA, PMPA, Loviride, and other dideoxyribonucleoside or fluorodideoxyribonuceoside; viral protease inhibitors, such as Saquinavir, Ritonavir, Indinavir, Nelfinavir, and VX-478; glycosidase inhibitors, such as SC-48334 and MDL-28574; viral mRNA capping inhibitors such as ribovirin; amphotericin B; ester bond binding molecule castanospermine with anti-HIV activity; hydroxyurea; glycoprotein processing inhibitors; glycosidase inhibitors SC-48334 and MDL-28574; virus absorbent; CD4 receptor blockers; chemokine co-receptor inhibitors; neutralizing antibody; integrase inhibitors and other fusion inhibitors.

Antiviral peptide is administered with other antiviral agents, including (but not limited to) drugs acting on different targets all through the virus replication process, such as reverse transcriptase inhibitors, viral protease inhibitors and glycosylation inhibitors, etc; antiviral agents acting on different targets all through the virus spreading process; antiviral agents acting on different sites of the same molecule; and antiviral agents capable of preventing or reducing the development of the drug resistance. The working mechanisms as well as the benefits of joint administration should be known to one of skill in the art.

The peptide of the present invention can be administered jointly with retrovirus inhibitors, including (but not limited to) nucleoside derivatives. The nucleoside derivatives are improved derivatives of purine nucleosides and pyrimidine nucleosides. Their acting mechanism is to prevent RNA and DNA from being synthesized. The nucleoside derivatives, in the absence of any 3'substituent that can be bound to other nucleosides, can suppress the synthesis of cDNA catalyzed by reverse transcriptase and thereby terminate the viral DNA replication. This is why they become anti-HIV therapeutic agents. For example, AZT and ddT, both of them can suppress HIV-1 replication in vivo and in vitro, had been approved as remedies for HIV infection and AIDS. However, use of these drugs for treatment can lead to mass propagation of drug-fast HIV strains in addition to many side effects.

The peptide of the present invention can be administered jointly with nucleoside derivatives and non-nucleoside derivatives. The nucleoside derivatives include (but not limited to): 2',3'-dideoxyadenosine (ddA); 2',3'-diseoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3'-azide2',3'-dideoxycytidine (AZT). According to an embodiment of the present invention, the nucleoside derivatives are halonucleoside, preferably 2',3'-dideoxy-2'-fluoronuceotides, including (but not limited to): 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytidine; and 2',3'-dideoxy-2',3'-didehydro-2'-fluoronuceotides, including (but not limited to): 2',3'-dideoxy-2',3'-didehydro-2'fluorothymidine (Fd4T). More preferably, the nucleoside derivatives are 2',3'-dideoxy-2'-fluoronuceotides wherein the fluorine bond is in the β conformation, including (but not limited to): 2',3'-dideoxy-2'α-fluoroadenosine (F-ddA), 2',3'-dideoxy-2'β-fluoroinosine (F-ddI), and 2',3'-dideoxy-2'β-fluorocytidine (F-ddC). Joint drug administration can reduce the dosage of nucleoside derivatives, and thereby reduce its toxicity as well as drug-resistance of the virus, while maintaining their antiviral activity.

According to a preferred embodiment of the present invention, the combination of effect dose of antiviral peptide and effect dose of nucleotide derivatives can be administered simultaneously or sequentially, including combination with AZT, ddC, and/or d4T in effective dose for the treatment of HIV infection. A more preferred drug combination includes (but not limited to): the antiviral peptide of present invention and ddT in effective dose; and/or 3TC, Viramune, Rescriptor, Sustiva, Loviride, Nevirapine, and Atevirdine in effective dose.

Antiviral peptide can also be administered jointly with inhibitors of urdine phosphorylating enzyme, including (but not limited to) acyclouridine compounds, including benzylacyclouridine (BAU); benzoxybenzylacyclouridine (BBAU); amethobenzylacyclouridine (AMBAU); amethobenzoxybenzylacyclouridine (AMB-BAU); hydroxymethylbenzylacyclouridine (HMBAU); and hydroxymethylbenzoxybenzylacyclouridine (HMBBAU).

The antiviral peptide of present invention can also be administered jointly with cytokines or cytokine inhibitors, including (but not limited to): rIFNα, rIFNβ, and rIFNγ; TNFα inhibitors, MNX-160, human rIFNα, human rIFNβ and human rIFNγ. A more preferred joint drug administration includes the peptide of the present invention and β interferon in effective dose.

Protease inhibitors prevent the virus from maturing mainly during the viral assembly period or after the assembly period (namely during the viral budding). Protease inhibitors show an antiviral activity both in vivo and in vitro. After being administered protease inhibitors, the AIDS patient HIV load exhibits an exponential decline and their CD4 lymphocytes rise in number (Deeks, et al. *JAMA* 277:145-53 (1997)). Joint administration of viral protease inhibitors with fusion inhibitor can produce a synergic effect and achieve satisfactory clinical results. The present invention provides a method for treating HIV infection, which is a joint drug administration using the antiviral peptide in effective dose together with a protease inhibitor in effective dose, the latter including (but not limited to): Indinavir, Invirase, Norvir, Viracept, and Agenerase.

In addition, antiviral peptide in the present invention can be administered jointly with amphotericin B. Amphotericin B is a polyene antifungal antibiotic that can bind irreversibly with sterol. Amphotericin B and its formate have an inhibiting effect against many lipid enveloped viruses including HIV. Amphotericin B has a serious toxicity towards human body while its formate has a much lower toxicity. Thus, Amphotericin B or its formate can be administered jointly with antiviral peptide, and produce an anti-HIV synergic effect, which allows clinical doctors to use Amphotericin B or its formate in lower doses without losing its antiviral activities.

The antiviral peptide of the present invention can also be administered jointly with the glycoprotein processing inhibitor castanospermine, which is a vegetable alkaloid capable of inhibiting glycol protein processing. HIV envelope contains two large glycoproteins gp120 and gp41. The glycosylation of proteins plays an important role in the interactions between gp120 and CD4. The progeny virus synthesized in the presence of castanospermine has a weaker infectivity than the parental virus. The joint administration of antiviral peptide or its derivatives with castanospermine can produce a synergic effect.

The therapeutic effect of the joint administration of antiviral peptide with the above-mentioned antiviral therapeutics can be evaluated by generally used methods in the present field. For example, the joint effect of antiviral peptide and AZT can be tested through a variety of in vitro experiments including: inhibiting HIV toxicity against cells, inhibiting the formation of synplasm, inhibiting the activity of reverse transcriptase, or inhibiting viral ability for RNA or protein synthesis, etc.

Method of preventing or treating HIV infection, including joint administration of antiviral peptide with at least one of other antiviral agents, such as reverse transcriptase inhibitors, protease inhibitors, mRNA processing inhibitors, protein glycosylation inhibitors, virus adsorbent, CD4 receptor inhibitors, chemokine co-receptor inhibitors, neutralizing antibody, integrase inhibitors, and other fusion inhibitors, including (but not limited to) nucleoside analogs or chain terminators; chemokine co-receptor inhibitors AMD-3100 (Tremblay, C. L. et al. *J. AIDS* 1:25(2)99-10 (2000))

According to an embodiment of the present invention, therapeutic agents that can be used jointly with antiviral peptide include (but not limited to): 2-deoxy-D-glucose (2dGlc), deoxynojirimycinacycloguanosine, virazole, rifadin, adamantanamine, rifabutine, ganciclover (DHPG), famciclove, buciclover (DHBG), fluoroiodoaracytosine, iodoxuridine, trifluorothymidine, ara-A, ara-AMP, bromovinyldeoxyuridine, BV-arau, 1-b-D-glycoarabinofuranoside-E-5-[2-bromovinyl]uracil, adamantethylamine, hydroxyurea, phenylacetic heptanedione, diarylamidine, (S)-(ρ-nitrobenzyl)-6-thioinosine and phosphonoformate. The present invention provides a drug combination of antiviral peptide with any other above-mentioned compounds.

In addition, the peptides of the present invention can also be used as a preventive measure for individuals who are exposed to HIV but have not been infected by it yet. Examples of such a preventive measure include (but not limited to): the prevention of mother-baby transmittal of the viruses; and the prevention of HIV infection in other situations, such as in medical workers handling HIV-contaminated blood, blood products, and body fluid in a medical accident. In these cases, the peptides of the present invention can be used as a preventive vaccine. With the inoculation of the peptide of the present invention, the host will produce antibodies that can inhibit HIV infection and neutralize HIV viruses.

The present invention provides a preventive vaccination scheme, which comprises: administering to the host the peptide of the present invention at an effective concentration for eliciting sufficient immune responses to neutralize the HIV, e.g., to develop the ability to inhibit HIV infection of cells. The elicited immune responses can be detected by standard techniques well-known to one of skill in the art. According to an embodiment of the present invention, the peptide used as vaccine is administered by muscle injection.

In order to increase immune responses, the peptide of the present invention can be administered with some proper adjuvants including (but not limited to): mineral gel, such as aluminium hydroxide; surface active substance, such as lysolecithin; Puronic polyhydric alcohol, polyanion; other peptides; oil emulsion agent; and other potential additives for human use, such as Bacillus Calmette-Guérin (BCG) and small coryneform. The routes by which the above-mentioned vaccine is administered include (but not limited to) oral, intradermal, intramuscular, intraperitoneal, intravenous, hypodermal, and mycteric routes.

Compared with existing drugs in the art, the present invention provides an antiviral combination and its preparation method. The combination can be used to prevent or treat HIV infection, it can suppress virus, and especially replication of virus in HIV infected people. The combination can improve $CD_4^+$ cells in infected people, which does contribute to the reconstruction of the immune system and recovery of the patients.

Examples are listed to demonstrate the preparation and activity of the pharmaceutical composition.

EXAMPLES

Example 1

Preparation of the Pharmaceutical Composition Containing the Antiviral Peptide FS-01

Pharmaceutical composition of the injection powder formulation containing antiviral peptide FS-01 was prepared in this implementing example. Quantified the loading agent, pH regulator and antiviral peptide as shown in the Tab. 1, then added sufficient quantity of water for injection to completely resolve the powder, after aseptic filtration and membrane filtration, FS-01 injection powder was finally obtained after freeze drying.

TABLE 1

Formulation of the composition containing the antiviral peptide (w/w)

| Material | Formulation A | Formulation B | Formulation C | Function |
|---|---|---|---|---|
| FS-01 (SEQ ID NO: 1) | 20% | 36% | 90% | Active component |
| Mannitol | 20% | 62% | 4% | Loading agent |
| $NaH_2PO_4 \cdot 2H_2O$ | 4% | 0 | 0 | pH regulator |
| $Na_2HPO_4 \cdot 12H_2O$ | 56% | 2% | 0 | |
| $Na_2CO_3$ | 0 | 0 | 8% | |

Example 2

Figure 1:
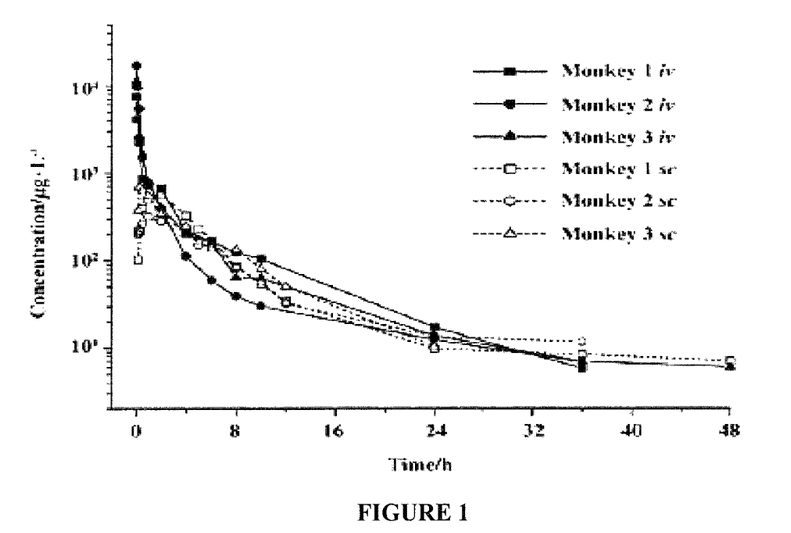
FIG. 1 shows the concentration-time curve in rhesus monkey after subcutaneous or intravenous injection of FS-01 (1.2 mg/kg). $T_{1/2}$ of FS-01 is 8.13±3.1 h, bioavailability (BA)= 50%, $T_{max}$=0.25 h-2 h, $C_{max}$=508.17±167.30 ng/ml (107.5±35.4 nM), $C_{24}$>9.8 ng/ml (2.07 nM).

Pharmacokinetic Study of Subcutaneous or Intravenous Injection of FS-01 in Rhesus Monkey FIG. 1 shows the result of the pharmacokinetic study of single subcutaneous or intravenous injection of FS-01 (1.2 mg/kg) in rhesus monkeys. $T_{1/2}$ of FS-01 is 8.13±3.1 h, BA=50%, $T_{max}$=0.25 h-2 h, $C_{max}$, 508.17±167.30 ng/ml (107.5±35.4 nM), $C_{24}$>9.8 ng/ml (2.07 nM).

Detailed experiment method as follows: three rhesus monkeys, crossover design, with a washout period of more than two weeks. Rhesus monkey was administrated 1.2 mg/kg of FS-01 by subcutaneously or intravenously injection, 1 ml of blood sample were collected at different point of time (0, 1, 5, 15, 30 min, 1, 2, 4, 6, 8, 12, 24 and 48 h). Drug concentration at different time point in blood sample was quantitatively analyzed by LC\MS\MS, utilizing iodine labeled FS-01 as internal standard, $C_{18}$ column, aqueous solution containing 0.1% TFA and acetonitrile as mobile phase. Pharmacokinetics analysis was carried out according to fitting model based on the concentration of FS-01, determined the half-life ($T_{1/2}$) in plasma, bioavailability and other pharmacokinetics parameters (FIG. 1).

Example 3

Figure 2:
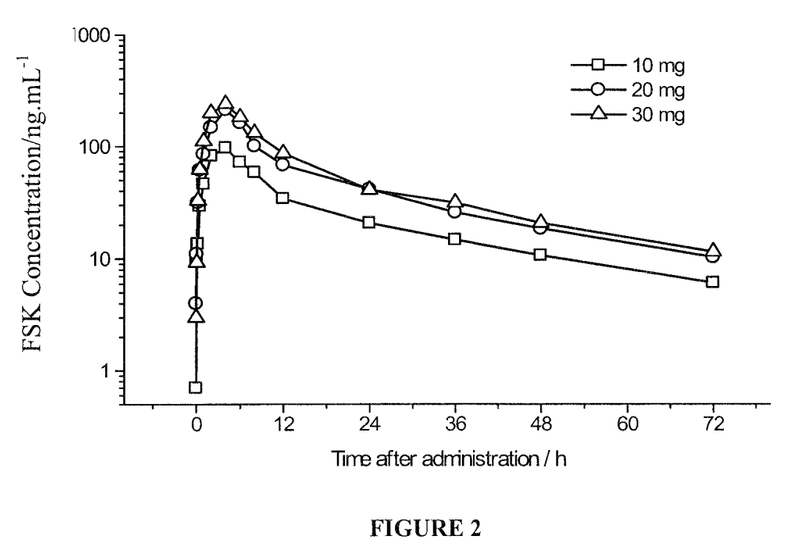
FIG. 2 shows the pharmacokinetic profile of the single subcutaneous injection of the pharmaceutical composition containing FS-01 in healthy volunteers. It demonstrated that clearance rate of FS-01 did not decrease as dose increasing, pharmacokinetic process is linear relation basically, $T_{1/2}$=20.0±18.6 h, $C_{max}$ in low, middle and high dose groups were 104±62 ng/ml (22.0±13.1 nM), 213±62 ng/ml (45.11±13.1 nM) and 250±197 ng/ml (52.9±41.7 nM) respectively, plasma drug concentration approached to baseline after 72 hours.

Pharmacokinetic Study of Single Injection of Pharmaceutical Composition Containing FS-01 in Healthy Volunteers 3-period crossover Latin square design was employed, 12 subjects were randomly divided into three groups, four subjects per group, and were sequentially abdomenal and subcutaneously injected by pharmaceutical composition containing 10, 20, 30 mg of FS-01, doses are listed in Table 2. Blood samples were collected at 30-5 min pre-dose, 5, 15, 30 min, 1, 2, 4, 6, 8, 12, 24, 48 and 72 h after injection. The concentration of FS-01 in blood sample was quantitatively analyzed by LC\MS\MS. The result shows (FIG. 2) that the rate at which a single injection of FS-01 cleared out the body did not slow down when the dosage increased, and the pharmacokinetic process basically exhibited a linear pattern with the $C_{max}$ in low, middle and high dose groups being 104±62 ng/ml (22.0±13.1 nM), 213±62 ng/ml (45.1±13.1 nM) and 250±197 ng/ml (52.9±41.7 nM) respectively, and plasma drug concentration approaching baseline after 72 hours.

TABLE 2

Design of pharmacokinetic study of single injection of pharmaceutical composition in healthy volunteers

| Groups | First Dose | Second Dose | Third Dose |
|---|---|---|---|
| I | 10 mg | 20 mg | 30 mg |
| II | 20 mg | 30 mg | 10 mg |
| III | 30 mg | 10 mg | 20 mg |

Example 4-Multidose administration of pharmaceutical composition containing FS-01 through subcutaneous injections in HIV positive patients Twenty-one subjects were divided into 5 groups, received pharmaceutical composition containing 1 mg, 5 mg, 10 mg, 20 mg, 30 mg FS-01 once daily, for 14 days. Determined the viral load before injection and after injection. The result (Table 3) showed that the viral load decreased in each group, and the significant drop initiated at 5 mg group. $CD_4^+$ cell count improved in each group. No signs of substantial side effects were observed in the subjects.

TABLE 3

Mean change of log value of viral load after multidose injection of pharmaceutical composition by subcutaneous in HIV infected patient

| Group | 1 mg | 5 mg | 10 mg | 20 mg | 30 mg |
|---|---|---|---|---|---|
| Subject (21) | 4 | 4 | 6 | 4 | 3 |
| Average change of VL, (log) | −0.07 | −0.76 | −0.47 | −0.89 | −0.3 |
| Average change of $CD_4^+$, (cells/mm³) | 30 | 102 | 29 | 46 | 73 |

Example 5

Multidose Administration of Pharmaceutical Composition Containing FS-01 Through Subcutaneous Injections in HIV Positive Patients Nineteen HIV patients were divided into two groups, were subcutaneously injected with pharmaceutical composition containing 10 mg and 20 mg of FS-01 once daily, for 28 days. The data was analyzed together with that in Example 4.

Figure 3:
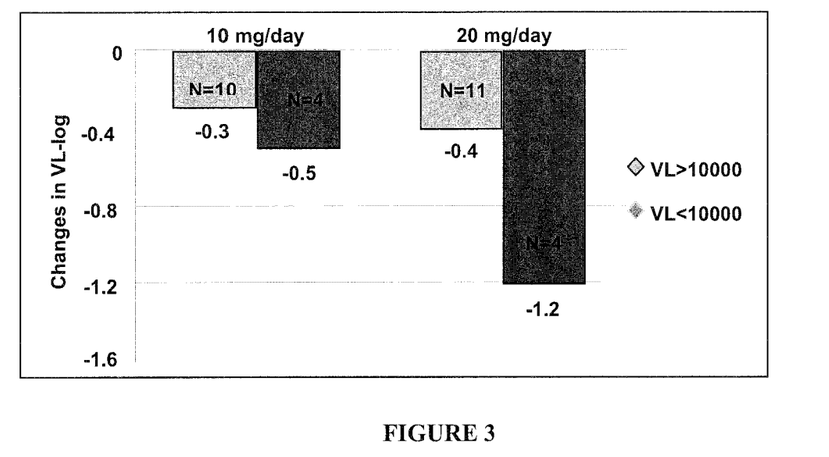
FIG. 3 is the diagram of log concentration of plasma viral load (VL) after subcutaneous injection of the pharmaceutical composition containing 10 mg and 20 mg of FS-01 in HIV patients. It demonstrated that viral load dropped in each group. In the same dose group, better efficacy is achieved in patients with viral load less than 10,000 c/ml. Viral load decreased by up to 1.2 log in 20 mg group.

It has been shown in the result that the pharmaceutical composition of the present invention has good safety profile. No signs of substantial side effects were observed in the patients. Plasma viral load in HIV infected patient with baseline less than <10,000 c/ml decreased by 1.2 log in 20 mg group 14 days after administration (see FIG. 3). And it is recommended for infected patient with baseline viral load more than 10,000 c/ml to receive combination treatment with other antiviral agents, such as antiretroviral inhibitors or protease inhibitors. The half-life of FS-01 at 20 mg in HIV patient is 39 hours.

Figure 4:
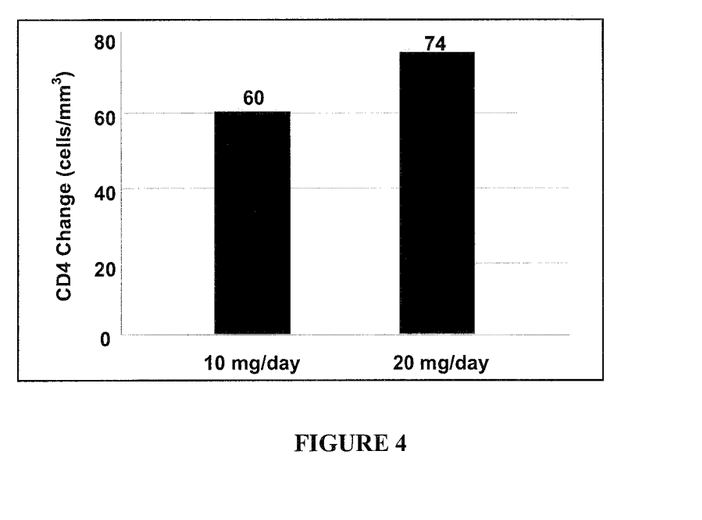
FIG. 4 is the change of $CD_4^+$ cell count by multidose of pharmaceutical composition containing 10 mg and 20 mg of FS-01 for four weeks. It showed a distinct increase of $CD_4^+$ cell count in HIV infected patients, and it is more prominent in higher dose.

It has been also shown that $CD_4^+$ cell count obviously increased in 10 mg and 20 mg dose groups, and the increase is more prominent in 20 mg group (see FIG. 4).

In conclusion, the pharmaceutical compositions of the present invention contain effective amount of antiviral peptide which effectively suppress HIV replication by decreasing HIV viral load and increasing CD4+ cell number in HIV patient. Purpose of preventing or treating HIV infection can be realized by administrating the pharmaceutical composition of the present invention, in different doses, with different dosing intervals and from different dosage routes, to maintain the effective concentration of antiviral peptide in human body.

We claim:

1. A pharmaceutical composition for treating HIV infection, comprising a therapeutically effective amount of an antiviral peptide comprising the amino acid sequence of:

```
                                              (SEQ ID NO: 1)
SWETWEREIENYTRQIYRILEESQEQQDRNERDLLE.
```

2. The pharmaceutical composition of claim 1, wherein the peptide comprises the sequence of:

```
X-SWETWEREIENYTRQIYRILEESQEQQDRNERDLLE -Z
``` wherein X is selected from the group consisting of an acetyl group, an amino group, a hydrophobic group, and a macromolecular carrier group; and wherein Z is selected from the group consisting of an amino group, a carboxyl group, a tert-butyloxycarbonyl group, a hydrophobic group, and a macromolecular carrier group.

3. The pharmaceutical composition of claim 2 wherein the hydrophobic group is selected from the group consisting of a carbobenzoxy, a dansyl, a tert-butyloxycarbonyl, and a 9-fluorenylmethyloxycarbonyl; and wherein the macromolecular carrier group is selected from the group consisting of a lipid-fatty acid chelate, a polyethylene glycol, and a carbohydrate.

4. The pharmaceutical composition of claim 1, wherein the peptide is of an amount selected from the group consisting of 1-100 mg, 3-90 mg, 5-80 mg, 7-70 mg, 9-60 mg, 10-50 mg, 15-20 mg, 1-15 mg, 5-15 mg, 20-25 mg, 25-30 mg, 25-100 mg, 30-90 mg, 35-80 mg, 40-70 mg, 45-60 mg, 3 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, and 100 mg.

5. The pharmaceutical composition of claim 1, wherein the peptide is 20%-90% (w/w) of the composition.

6. The pharmaceutical composition of claim 1, comprising a sterile injection powder.

7. The pharmaceutical composition of claim 1, comprising a lyophilized injection powder.

8. The pharmaceutical composition of claim 1, further comprising another antiviral agent.

9. The pharmaceutical composition of claim 1, further comprising one or more agents selected from the group consisting of reverse transcriptase inhibitors, viral protease inhibitors, glycosidase inhibitors, viral mRNA capping inhibitors, amphotericin B, ester-bond binding molecules with anti-HIV activity, hydroxyurea, α-interferon, β-interferon, γ-interferon, and other anti-HIV agents.

10. A method for preparing a pharmaceutical composition, the method comprising adding to the composition an antiviral peptide comprising the amino acid sequence of:

```
                                              (SEQ ID NO: 1)
SWETWEREIENYTRQIYRILEESQEQQDRNERDLLE.
```

11. The method of claim 10, further comprising adding another antiviral agent.

12. The method of claim 10, further comprising adding at least one component selected from the group consisting of reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, γ-interferon, and other anti-HIV agents.

13. The method of claim 10, wherein the peptide is of an amount between about 1 and about 100 mg.

14. The method of claim 10, wherein the peptide is 20%-90% of the composition by weight.

15. A method of treating an HIV infection, comprising administering to a subject in need thereof an effective amount of a peptide comprising the amino acid sequence of:

```
                                              (SEQ ID NO: 1)
SWETWEREIENYTRQIYRILEESQEQQDRNERDLLE.
```

16. The method of claim 15, comprising administering to the subject the peptide at an interval selected from the group consisting of: twice daily, once daily, once every two days, every three days, every four days, every five days, every six days, and every seven days.

17. The method of claim 15, comprising administering to the subject the peptide no more frequently than once a day.

18. The method of claim 15, further comprising administering to the subject at least a second antiviral agent.

19. The method of claim 18, wherein the second antiviral agent is selected from the group consisting of reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, γ-interferon, and other anti-HIV agents.

20. The method of claim 18 wherein the second antiviral agent is administered at about the same time as the peptide comprising the amino acid sequence of SEQ ID NO: 1.

21. The method of claim 18 wherein the second antiviral agent is administered at a substantial interval to the peptide comprising the amino acid sequence of SEQ ID NO:1.

22. The method of claim 15, wherein the peptide is administered such that the plasma concentration of the peptide in the patient reaches between about 1 and about 250 nM.

23. The method of claim 15, wherein the plasma concentration of the peptide in the patient reaches a value selected from the group consisting of: 5-250 nM, 10-220 nM, 25-200 nM, 30-180 nM, 35-160 nM, 40-140 nM, 45-120 nM, 50-100 nM, 60-90 nM, 70-80 nM, 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 220 nM, and 250 nM.

24. The method of claim 15, further comprising selecting the subject such that the HIV viral load in the subject's blood is below a clinically acute level.

25. The method of claim 15, further comprising selecting the subject such that the HIV viral load in the subject's blood is at or below 30,000 copies per milliliter.

26. The method of claim 15, wherein the peptide is administered in a manner selected from the group consisting of intramuscular, intravenous, subcutaneous, oral, mucosal, rectal and percutaneous administration.

27. The pharmaceutical composition of claim 1, wherein the amount of the peptide is about 20 mg.

* * * * *